United States Patent
Shirwan

(10) Patent No.: US 12,023,367 B2
(45) Date of Patent: Jul. 2, 2024

(54) IMMUNOMODULATION FOR THE LONG TERM PREVENTION AND TREATMENT OF AUTOIMMUNE DISEASES AND FOREIGN TISSUE REJECTION

(71) Applicants: University of Louisville Research Foundation, Inc., Louisville, KY (US); The Curators of the University of Missouri, Columbia, MO (US)

(72) Inventor: Haval Shirwan, Columbia, MO (US)

(73) Assignees: UNIVERSITY OF LOUISVILLE RESEARCH FOUNDATION, INC., Louisville, KY (US); THE CURATORS OF THE UNIVERSITY OF MISSOURI, Columbia, MO (US)

( * ) Notice: Subject to any disclaimer, the term of this patent is extended or adjusted under 35 U.S.C. 154(b) by 1356 days.

(21) Appl. No.: 15/736,088

(22) PCT Filed: Jun. 17, 2016

(86) PCT No.: PCT/US2016/038185
§ 371 (c)(1),
(2) Date: Dec. 13, 2017

(87) PCT Pub. No.: WO2016/205714
PCT Pub. Date: Dec. 22, 2016

(65) Prior Publication Data
US 2018/0318394 A1 Nov. 8, 2018

Related U.S. Application Data

(60) Provisional application No. 62/181,815, filed on Jun. 19, 2015.

(51) Int. Cl.
| | | |
|---|---|---|
| *A61K 38/20* | (2006.01) | |
| *A61K 35/12* | (2015.01) | |
| *A61K 35/26* | (2015.01) | |
| *A61K 35/39* | (2015.01) | |
| *A61K 38/17* | (2006.01) | |
| *A61K 39/00* | (2006.01) | |
| *A61K 39/385* | (2006.01) | |
| *A61K 45/06* | (2006.01) | |
| *A61K 47/69* | (2017.01) | |
| *A61P 37/06* | (2006.01) | |
| *A61P 43/00* | (2006.01) | |
| *A61K 31/35* | (2006.01) | |
| *A61K 31/675* | (2006.01) | |

(52) U.S. Cl.
CPC .......... *A61K 38/2013* (2013.01); *A61K 35/12* (2013.01); *A61K 35/26* (2013.01); *A61K 35/39* (2013.01); *A61K 38/177* (2013.01); *A61K 39/0008* (2013.01); *A61K 39/385* (2013.01); *A61K 45/06* (2013.01); *A61K 47/6901* (2017.08); *A61P 37/06* (2018.01); *A61P 43/00* (2018.01); *A61K 31/35* (2013.01); *A61K 31/675* (2013.01); *A61K 2039/577* (2013.01); *A61K 2039/58* (2013.01)

(58) Field of Classification Search
None
See application file for complete search history.

(56) References Cited

U.S. PATENT DOCUMENTS

| | | | |
|---|---|---|---|
| 7,745,215 B2 | 6/2010 | Shirwan | |
| 7,927,602 B2 | 4/2011 | Shirwan | |
| 8,076,096 B2 | 12/2011 | Shirwan | |
| 8,551,494 B2 | 10/2013 | Shirwan | |
| 9,255,133 B2 | 2/2016 | Shirwan | |
| 2003/0078228 A1 | 4/2003 | Taylor et al. | |
| 2003/0135789 A1 | 7/2003 | Dewitt et al. | |
| 2004/0018170 A1 | 1/2004 | Shirwan | |
| 2007/0172947 A1 | 7/2007 | Shirwan | |
| 2011/0052529 A1 | 3/2011 | Shirwan | |
| 2011/0081369 A1 | 4/2011 | Shirwan | |
| 2012/0213730 A1 | 8/2012 | Shirwan | |
| 2013/0224145 A1 | 8/2013 | Wang | |
| 2014/0314866 A1 | 10/2014 | Brusko et al. | |
| 2015/0086506 A1 | 3/2015 | Shirwan | |

FOREIGN PATENT DOCUMENTS

| | | |
|---|---|---|
| JP | 2014-141527 A | 8/2014 |
| WO | WO-2012/123381 A1 | 9/2012 |

OTHER PUBLICATIONS

Yolcu et al. Pancreatic islets engineered with SA-FasL protein establish robust localized tolerance by inducing regulatory T cells in mice. J Immunol 187: 5901-5909, 2011.*
Ginberg-Bleyer et al. (2010) J. Exp. Medicine 9: 1871-1878.*
Askenasy et al., "Induction of tolerance using Fas ligand: a double-edged immunomodulator," Blood, vol. 105, No. 4 (available online Oct. 2004), pp. 1396-1404, XP055576160.
Esser et al., "IL-2 induces Fas Ligand/Fas (CD95L/CD95) cytotoxicity in CD8+ and CD4+ T lymphocyte clones," The Journal of Immunology, (Jun. 1997), pp. 5612-5618, XP055576718.
Franke et al., "A novel multimeric form of FasL modulates the ability of diabetogenic T cells to mediate type 1 diabetes in an adoptive transfer model," Molecular Immunology 44 (Available online Feb. 2007) 2884-2892, XP005938372.
Rafaeli et al., "Biochemical Mechanisms of IL-2-Regulated Fas-Mediated T Cell Apoptosis," Immunity, vol. 8, 615-623 (May 1998) XP055576709.
Bulfone-Paus et al., "An interleukin-2-IgG-Fas ligand fusion protein suppresses delayed-type hypersensitivity in mice by triggering apoptosis in activated T cells as a novel strategy for immunosuppression" Transplantation, vol. 69, No. 7, pp. 1386-1391 (2000).

\* cited by examiner

*Primary Examiner* — Michael D Pak
(74) *Attorney, Agent, or Firm* — Foley & Lardner LLP

(57) ABSTRACT

Described herein are pharmaceutical compositions, medicaments and methods for providing effective immunomodulation with chimeric proteins including FasL moieties for selective and long-lasting regulation of the immune response.

9 Claims, 21 Drawing Sheets

Specification includes a Sequence Listing.

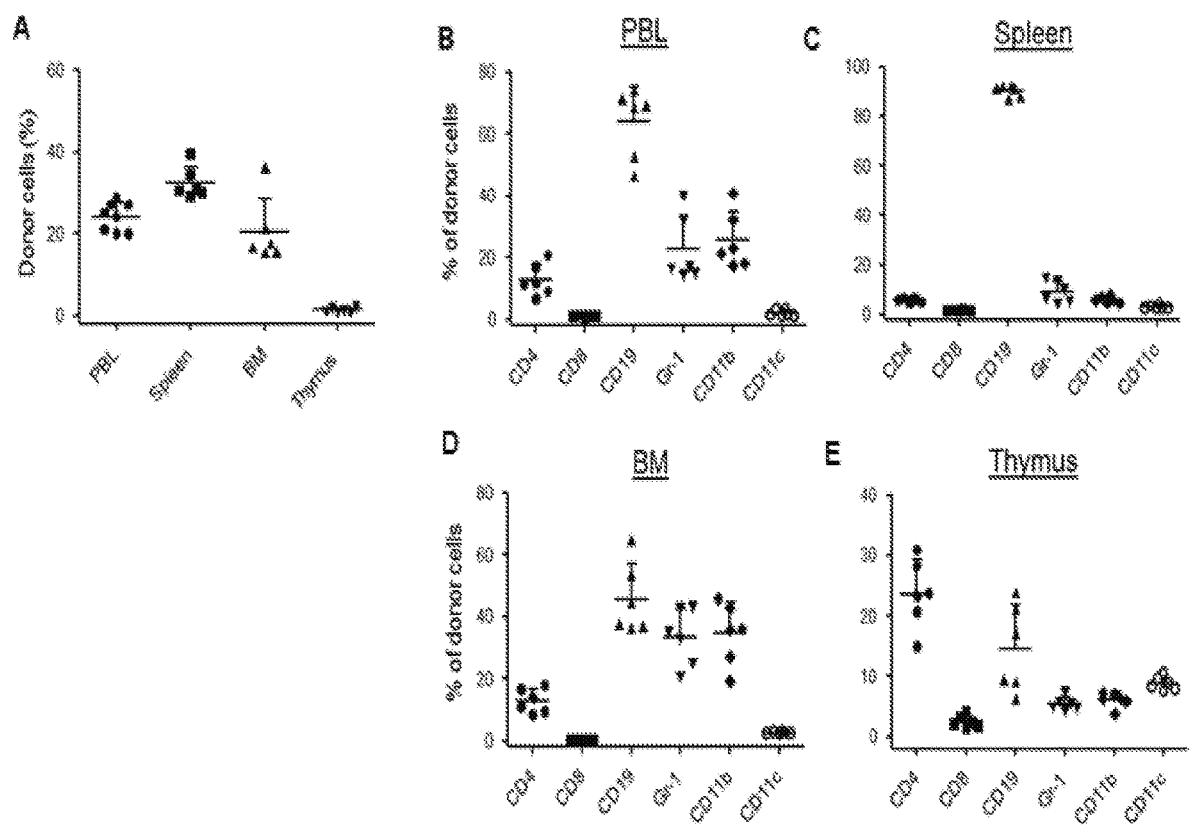
Fig. 13A-E

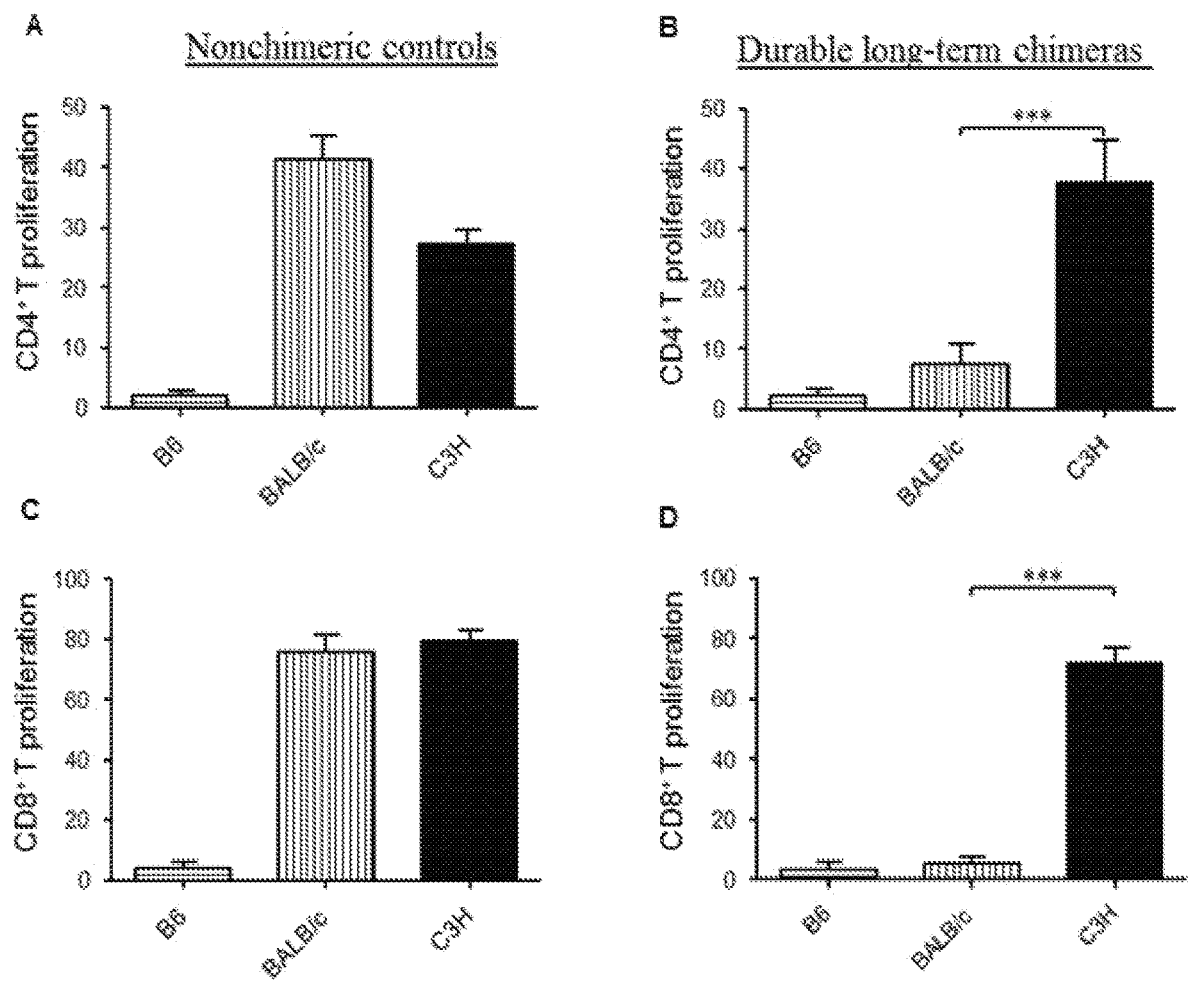
Fig. 14A-D

FIG. 15
Human SA-FasL Nucleotide Construct: 1xFLAG-4G-FasL
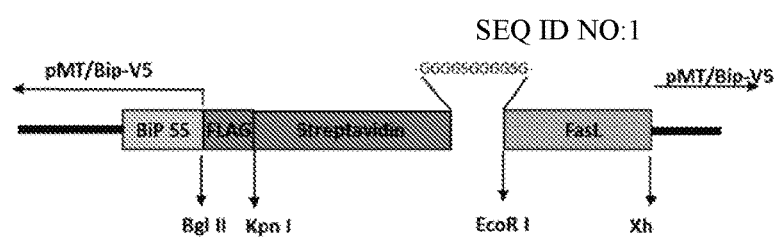
Bgl II-FLAG-Kpn1-SA-4G-EcoR1-huFasLed(131-181)-Xho1
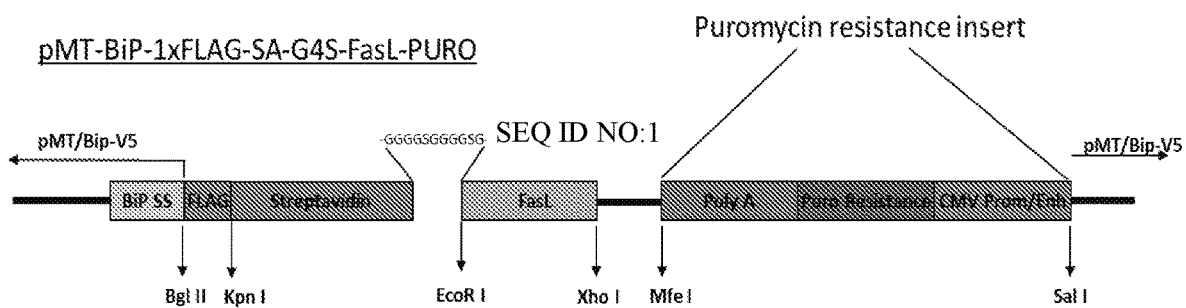

FIG. 16A

Human SA-FasL Nucleotide Sequence: 1xFLAG-4G-FasL (SEQ ID NO:2)

AGATCTGATTACAAGGATGACGATGACAAGGGTACCATCACCGGCACCTGGTACAACCAGCTCG
GCTCGACCTTCATCGTGACCGCGGGCGCCGATGGCGCCCTGACCGGAACCTACGAGTCGGCCGT
CGGCAACGCCGAGAGCCGCTACGTCCTGACCGGTCGTTACGACAGCGCCCCGGCCACCGACGGC
AGCGGCACCGCCCTCGGTTGGACGGTGGCCTGGAAGAATAACTACCGCAACGCCCACTCCGCGA
CCACGTGGAGCGGCCAGTACGTCGGCGGCGCCGAGGCGAGGATCAACACCCAGTGGCTGTTGAC
CTCCGGCGCCACCGAGGCCAACGCCTGGAAGTCCACGCTGGTCGGCCACGACACCTTCACCAAG
GTGAAGCCGTCCGCCGCCTCAAGCGGAGGAGGAGGATCAGGAGGAGGAGGATCAGGAGAATTCA
TAGGCCACCCCAGTCCACCCCCTGAAAAAAAGGAGCTGAGGAAAGTGGCCCATTTAACAGGCAA
GTCCAACTCAAGGTCCATGCCTCTGGAATGGGAAGACACCTATGGAATTGTCCTGCTTTCTGGA
GTGAAGTATAAGAAGGGTGGCCTTGTGATCAATGAAACTGGGCTGTACTTTGTATATTCCAAAG
TATACTTCCGGGGTCAATCTTGCAACAACCTGCCCCTGAGCCACAAGGTCTACATGAGGAACTC
TAAGTATCCCCAGGATCTGGTGATGATGGAGGGGAAGATGATGAGCTACTGCACTACTGGGCAG
ATGTGGGCCCGCAGCAGCTACCTGGGGGCAGTGTTCAATCTTACCAGTGCTGATCATTTATATG
TCAACGTATCTGAGCTCTCTCTGGTCAATTTTGAGGAATCTCAGACGTTTTTCGGCTTATATAA
GCTTTAATAG<u>CTCGAG</u>

FIG. 16B

Human SA-FasL Protein Sequence: 1xFLAG-4G-FasL (SEQ ID NO:3)

R S D Y K D D D D K G T I T G T W Y N Q L G S T F I V T A G A D
G A L T G T Y E S A V G N A E S R Y V L T G R Y D S A P A T D G
S G T A L G W T V A W K N N Y R N A H S A T T W S G Q Y V G G A
E A R I N T Q W L L T S G A T E A N A W K S T L V G H D T F T K
V K P S A A S S G G G G S G G G G S G E F I G H P S P P P E K K
E L R K V A H L T G K S N S R S M P L E W E D T Y G I V L L S G
V K Y K K G G L V I N E T G L Y F V Y S K V Y F R G Q S C N N L
P L S H K V Y M R N S K Y P Q D L V M M E G K M M S Y C T T G Q
M W A R S S Y L G A V F N L T S A D H L Y V N V S E L S L V N F
E E S Q T F F G L Y K L Stop Stop L E SA= 124 AA; huFasLed = 152 AA; linker = 22 AA; RS = 6 AA: 304 AA.
SA-huFasL construct = 304 AA, which translates to ~ <u>34</u> kDa.
FlagTag SA Linker FasL.

FIG. 17A

Rat SA-FasL Nucleotide Sequence: 1xFLAG-4G-FasL (SEQ ID NO:4)

TCGCGCGTTTCGGTGATGACGGTGAAAACCTCTGACACATGCAGCTCCCGGAGACGGTCACAGC
TTGTCTGTAAGCGGATGCCGGGAGCAGACAAGCCCGTCAGGGCGCGTCAGCGGGTGTTGGCGGG
TGTCGGGGCTGGCTTAACTATGCGGCATCAGAGCAGATTGTACTGAGAGTGCACCATATGCGGT
GTGAAATACCGCACAGATGCGTAAGGAGAAAATACCGCATCAGGCGCCATTCGCCATTCAGGCT
GCGCAACTGTTGGGAAGGGCGATCGGTGCGGGCCTCTTCGCTATTACGCCAGCTGGCGAAAGGG
GGATGTGCTGCAAGGCGATTAAGTTGGGTAACGCCAGGGTTTTCCCAGTCACGACGTTGTAAAA
CGACGGCCAGTGCCAGTGAATTTTAACGTTGCAGGACAGGATGTGGTGCCCGATGTGACTAGCT
CTTTGCTGCAGGCCGTCCTATCCTCTGGTTCCGATAAGAGACCCAGAACTCCGGCCCCCCACCG
CCCACCGCCACCCCCATACATATGTGGTACGCAAGTAAGAGTGCCTGCGCATGCCCATGTGCC
CCACCAAGAGTTTTGCATCCCATACAAGTCCCCAAAGTGGAGAACCGAACCAATTCTTCGCGGG
CAGAACAAAAGCTTCTGCACACGTCTCCACTCGAATTTGGAGCCGGCCGGCGTGTGCAAAAGAG
GTGAATCGAACGAAAGACCCGTGTGTAAAGCCGCGTTTCCAAAATGTATAAAACCGAGAGCATC
TGGCCAATGTGCATCAGTTGTGGTCAGCAGCAAAATCAAGTGAATCATCTCAGTGCAACTAAAG
GGGGGATCCGATCTCAATATGAAGTTATG<u>CATATTACTGGCCGTCGT</u>GGC<u>C</u>TTTGTTGGCCTCT
CGCTCGGGAGATCTGATTACAAGGATGACGATGACAAG<u>GGTACC</u>ATCACCGGCACCTGGTACAA
CCAGCTCGGCTCGACCTTCATCGTGACCGCGGGCGCCGATGGCGCCCTGACCGGAACCTACGAG
TCGGCCGTCGGCAACGCCGAGAGCCGCTACGTCCTGACCGGTCGTTACGACAGCGCCCCGGCCA
CCGACGGCAGCGGCACCGCCCTCGGTTGGACGGTGGCCTGGAAGAATAACTACCGCAACGCCCA
CTCCGCGACCACGTGGAGCGGCCAGTACGTCGGCGGCGCCGAGGCGAGGATCAACACCCAGTGG
CTGTTGACCTCCGGCGCCACCGAGGCCAACGCCTGGAAGTCCACGCTGGTCGGCCACGACACCT
TCACCAAGGTGAAGCCGTCCGCCGCCTCAAGCGGAGGAGGAGGATCAGGAGGAGGAGGATCAGG
A<u>GAATTC</u>atagccaacccccagcacaccctctgaaaccaaaaagccaaggagtgtggcccactta
acagggaaccccgctcaaggtccatccctctggaatgggaagacacatatggaactgctttga
tctctggagtgaagtataagaaaggcggccttgtgatcaatgaggctggggttgtacttcgtata
ttccaaagtatacttccggggtcagtcttgcaacagccagcccctaagccacaaggtctatatg
aggaactttaagtatcctggggatctggtgctaatggaggagaagaagttgaattactgcacta
ctggccagatatgggcccacagcagctacctaggggcagtatttaatcttaccgttgctgacca
tttatatgtcaacatatctcaactctctctgatcaattttgaggaatctaagaccttttttggc
ttatataagctttaa<u>CTCGAG</u>TCTAGAGGGCCCTTCGAAGGTAAGCCTATCCCTAACCCTCTCC
TCGGTCTCGATTCTACGCGTACCGGTCATCATCACCATCACCATTGAGTTTAAACCCG<u>CTGATC
AGCCTCGACTGT</u>GCCTTCTAAGGCCTGAGCTCGCTGATCAGCCTCGATCGAGGATCCAGACATG
ATAAGATACATTGATGAGTTTGGACAAACCACAACTAGAATGCAGTGAAAAAAATGCTTTATTT
GTGAAATTTGTGATGCTATTGCTTTATTTGTAACCATTATAAGCTGCAATAAACAAGTTAACAA
CAAC<u>AATTGCTAAAATACAGCATAGCAAAACTTTAACCTCCAAATCAAGCCTCTACTTGAATCC</u>
TTTTCTGAGGGATGAATAAGGCATAGGCATCAGGGGCTGTTGCCAATGTGCATTAGCTGTTTGC
AGCCTCACCTTCTTTCATGGAGTTTAAGATATAGTGTATTTTCCCAAGGTTTGAACTAGCTCTT
CATTTCTTTATGTTTTAAATGCACTGACCTCCCACATTCCCTTTTTAGTAAAATATTCAGAAAT
AATTTAAATACATCATTGCAATGAAAATAAATGTTTTTTATTAGGCAGAATCCAGATGCTCAAG
GCCCTTCATAATATCCCCAGTTTAGTAGTTGGACTTAGGGAACAAAGGAACCTTTAATAGAAA
TTGGACAGCAAGAAAGCGAGCTTCTAGCTCAGGTTTAAGCTCCAGGCTTCCTTGTCATGCACCA
AGTTCTTGGGCCTTCTGGAACCTCAACATCAGCTGTCACAGTGAATCCCAGTCTTTCATAAAAA
GGCAGGTTTCTGGGAGCAGAAGTTTCCAGAAAGGCAGGAACTCCAGCCCTTTCAGCAGCTTCAA
CTCCAGGCAGAACAACAGCAGATCCCAGACCCTTTCCCTGGTGGTCAGGGCTCACTCCAACAGT

FIG. 17A (cont.)

```
TGCCAGAAACCAAGCTGGCTCTTTTGGCCTGTGTGGTGCCAGCAGACCTTCCATTTGTTGTTGT
GCTGCCAGCCTGCTTCCAGAGAGCTCAGCCATTCTTGGTCCAATTTCAGCAAAAACAGCACCAG
CTTCAACAGACTCAGGTGTTGTCCAAACTGCAACAGCAGCTCCATCATCTGCAACCCAAACTTT
TCCAATGTCCAGTCCCACTCTGGTGAGGAAGAGTTCTTGCAGTTCTGTCACCCTCTCAATGTGC
CTGTCAGGGTCAACTGTGTGCCTTGTTGCAGGGTAGTCTGCAAAAGCAGCAGCCAGTGTTCTCA
CAGCTCTTGGAACATCATCTCTGGTTGCCAGCCTCACTGTGGGTTTGTACTCAGTCATGGTGGC
CCTCCTATAGTGAGTCGTATTATACTATGCCGATATACTATGCCGATGATTAATTGTCAAAACA
GCGTGGATGGCGTCTCCAGCTTATCTGACGGTTCACTAAACGAGCTCTGCTTATATAGACCTCC
CACCGTACACGCCTACCGCCCATTTGCGTCAATGGGGCGGAGTTGTTACGACATTTTGGAAAGT
CCCGTTGATTTACTAGTCAAAACAAACTCCCATTGACGTCAATGGGGTGGAGACTTGGAAATCC
CCGTGAGTCAAACCGCTATCCACGCCCATTGATGTACTGCCAAAACCGCATCATCATGGTAATA
GCGATGACTAATACGTAGATGTACTGCCAAGTAGGAAAGTCCCATAAGGTCATGTACTGGGCAT
AATGCCAGGCGGGCCATTTACCGTCATTGACGTCAATAGGGGCGTACTTGGCATATGATACAC
TTGATGTACTGCCAAGTGGGCAGTTTACCGTAAATACTCCACCCATTGACGTCAATGGAAAGTC
CCTATTGGCGTTACTATGGGAACATACGTCATTATTGACGTCAATGGGCGGGGGTCGTTGGGCG
GTCAGCCAGGCGGGCCATTTACCGTAAGTTATGTAACGCCTGCGTCGACCTGCAGGCATGCAAG
CTTGGCGTAATCATGGTCATAGCTGTTTCCTGTGTGAAATTGTTATCCGCTCACAATTCCACAC
AACATACGAGCCGGAAGCATAAAGTGTAAAGCCTGGGGTGCCTAATGAGTGAGCTAACTCACAT
TAATTGCGTTGCGCTCACTGCCCGCTTTCCAGTCGGGAAACCTGTCGTGCCAGCTGCATTAATG
AATCGGCCAACGCGCGGGGAGAGGCGGTTTGCGTATTGGGCGCTCTTCCGCTTCCTCGCTCACT
GACTCGCTGCGCTCGGTCGTTCGGCTGCGGCGAGCGGTATCAGCTCACTCAAAGGCGGTAATAC
GGTTATCCACAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTTACCGGATACCTGTC
CGCCTTTCTCCCTTCGGGAAGCGTGGCGCTTTCTCATAGCTCACGCTGTAGGTATCTCAGTTCG
GTGTAGGTCGTTCGCTCCAAGCTGGGCTGTGTGCACGAACCCCCCGTTCAGCCCGACCGCTGCG
CCTTATCCGGTAACTATCGTCTTGAGTCCAACCCGGTAAGACACGACTTATCGCCACTGGCAGC
AGCCACTGGTAACAGGATTAGCAGAGCGAGGTATGTAGGCGGTGCTACAGAGTTCTTGAAGTGG
TGGCCTAACTACGGCTACACTAGAAGGACAGTATTTGGTATCTGCGCTCTGCTGAAGCCAGTTA
CCTTCGGAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGATCTTT
TCTACGGGGTCTGACGCTCAGTGGAACGAAAACTCACGTTAAGGGATTTTGGTCATGAGATTAT
CAAAAAGGATCTTCACCTAGATCCTTTTAAATTAAAAATGAAGTTTTAAATCAATCTAAAGTAT
ATATGAGTAAACTTGGTCTGACAGTTACCAATGCTTAATCAGTGAGGCACCTATCTCAGCGATC
TGTCTATTTCGTTCATCCATAGTTGCCTGACTCCCCGTCGTGTAGATAACTACGATACGGGAGG
GCTTACCATCTGGCCCCAGTGCTGCAATGATACCGCGAGACCCACGCTCACCGGCTCCAGATTT
ATCAGCAATAAACCAGCCAGCCGGAAGGGCCGAGCGCAGAAGTGGTCCTGCAACTTTATCCGCC
TCCATCCAGTCTATTAATTGTTGCCGGGAAGCTAGAGTAAGTAGTTCGCCAGTTAATAGTTTGC
GCAACGTTGTTGCCATTGCTACAGGCATCGTGGTGTCACGCTCGTCGTTTGGTATGGCTTCATT
CAGCTCCGGTTCCCAACGATCAAGGCGAGTTACATGATCCCCATGTTGTGCAAAAAGCGGTT
AGCTCCTTCGGTCCTCCGATCGTTGTCAGAAGTAAGTTGGCCGCAGTGTTATCACTCATGGTTA
TGGCAGCACTGCATAATTCTCTTACTGTCATGCCATCCGTAAGATGCTTTTCTGTGACTGGTGA
GTACTCAACCAAGTCATTCTGAGAATAGTGTATGCGGCGACCGAGTTGCTCTTGCCCGGCGTCA
ATACGGGATAATACCGCGCCACATAGCAGAACTTTAAAAGTGCTCATCATTGGAAAACGTTCTT
CGGGGCGAAAACTCTCAAGGATCTTACCGCTGTTGAGATCCAGTTCGATGTAACCCACTCGTGC
ACCCAACTGATCTTCAGCATCTTTTACTTTCACCAGCGTTTCTGGGTGAGCAAAAACAGGAAGG
```

FIG. 17A (cont.)

CAAAATGCCGCAAAAAGGGAATAAGGGCGACACGGAAATGTTGAATACTCATACTCTTCCTTT
TTCAATATTATTGAAGCATTTATCAGGGTTATTGTCTCATGAGCGGATACATATTTGAATGTAT
TTAGAAAAATAAACAAATAGGGGTTCCGCGCACATTTCCCCGAAAAGTGCCACCTGACGTCTAA
GAAACCATTATTATCATGACATTAACCTATAAAAATAGGCGTATCACGAGGCCCTTTCGT

FIG. 17B

Rat SA-FasL Protein Sequence: 1xFLAG-4G-FasL (SEQ ID NO:5)

R S D Y K D D D D K G T I T G T W Y N Q L G S T F I V T A G A D G A L T G T Y E S A V G N A E S R Y V
L T G R Y D S A P A T D G S G T A L G W T V A W K N N Y R N A H S A T T W S G Q Y V G G A E A R I N
T Q W L L T S G A T E A N A W K S T L V G H D T F T K V K P S A A S S G G G G S G G G G S G E F I A N
P S T P S E T K K P R S V A H L T G N P R S R S I P L E W E D T Y G T A L I S G V K Y K K G G L V I N E
A G L Y F V Y S K V Y F R G Q S C N S Q P L S H K V Y M R N F K Y P G D L V L M E E K K L N Y C T T
G Q I W A H S S Y L G A V F N L T V A D H L Y V N I S Q L S L I N F E E S K T F F G L Y K L Stop L E Flag Tag  SA  Linker FasL

FIG. 18A

Human SA-IL-2 Construct

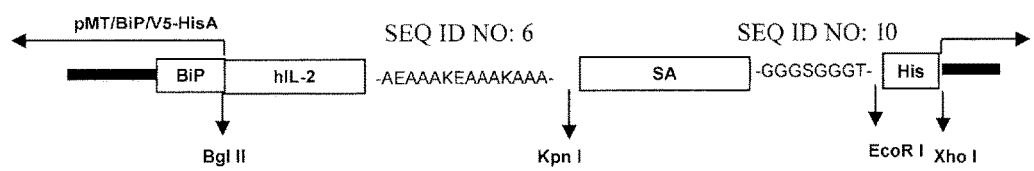

Bgl II-hIL2- Ala3-Kpn 1-SA-linker-EcoR1-HisA-Xho1

FIG. 18B

Human SA-IL-2 Un-optimized DNA Sequence (SEQ ID NO : 7)

AGATCTGCACCTACTTCAAGTTCTACAAAGAAAACACAGCTACAACTGGAGCATTTACTGCTGG
ATTTACAGATGATTTTGAATGGAATTAATAATTACAAGAATCCCAAACTCACCAGGATGCTCAC
ATTTAAGTTTTACATGCCCAAGAAGGCCACAGAACTGAAACATCTTCAGTGTCTAGAAGAAGAA
CTCAAACCTCTGAAGGAAGTGCTAAATTTAGCTCAAAGCAAAAACTTTCACTTAAGACCCAGGG
ACTTAATCAGCAATATCAACGTAATAGTTCTGGAACTAAAGGGATCTGAAACAACATTCATGTG
TGAATATGCTGATGAGACAGCAACCATTGTAGAATTTCTGAACAGATGGATTACCTTTTCTCAA
AGCATCATCTCAACACTAACTGCTGAAGCTGCAGCTAAAGAAGCTGCAGCTAAAGCTGCTGCTG
GTACCATCACCGGCACCTGGTACAACCAGCTCGGCTCGACCTTCATCGTGACCGCGGGCGCCGA
TGGCGCCCTGACCGGAACCTACGAGTCGGCCGTCGGCAACGCCGAGAGCCGCTACGTCCTGACC
GGTCGTTACGACAGCGCCCCGGCCACCGACGGCAGCGGCACCGCCCTCGGTTGGACGGTGGCCT
GGAAGAATAACTACCGCAACGCCCACTCCGCGACCACGTGGAGCGGCCAGTACGTCGGCGGCGC
CGAGGCGAGGATCAACACCCAGTGGCTGTTGACCTCCGGCGCCACCGAGGCCAACGCCTGGAAG
TCCACGCTGGTCGGCCACGACACCTTCACCAAGGTGAAGCCGTCCGCCGCCTCAAGCGGAGGCG
GTGGATCAGGTGGAGGCCATCATCACCATCACCATGAATTC CTCGAG

FIG. 18C

Human SA-IL-2 Un-optimized DNA Sequence (SEQ ID NO : 8)

```
AGATCTGCAC CTACTTCAAG TTCTACAAAG AAAACACAGC TACAACTGGA
GCATTTACTG CTGGATTTAC AGATGATTTT GAATGGAATT AATAATTACA
AGAATCCCAA ACTCACCAGG ATGCTACAT TTAAGTTTTA CATGCCCAAG
AAGGCCACAG AACTGAAACA TCTTCAGTGT CTAGAAGAAG AACTCAAACC
TCTGAAGGAA GTGCTAAATT TAGCTCAAAG CAAAAACTTT CACTTAAGAC
CCAGGGACTT AATCAGCAAT ATCAACGTAA TAGTTCTGGA ACTAAAGGGA
TCTGAAACAA CATTCATGTG TGAATATGCT GATGAGACAG CAACCATTGT
AGAATTTCTG AACAGATGGA TTACCTTTTC TCAAAGCATC ATCTAACAC
TAACTGCTGA AGCTGCAGCT AAAGAAGCTG CAGCTAAAGC TGCTGCTGGT
ACCATCACCG GCACCTGGTA CAACCAGCTC GGCTCGACCT TCATCGTGAC
CGCGGGCGCC GATGGCGCCC TGACCGGAAC CTACGAGTCG GCCGTCGGCA
ACGCCGAGAG CCGCTACGTC CTGACCGGTC GTTACGACAG CGCCCCGGCC
ACCGACGGCA GCGGCACCGC CCTCGGTTGG ACGGTGGCCT GGAAGAATAA
CTACCGCAAC GCCCACTCCG CGACCACGTG GAGCGGCCAG TACGTCGGCG
GCGCCGAGGC GAGGATCAAC ACCCAGTGGC TGTTGACCTC CGGCGCCACC
GAGGCCAACG CCTGGAAGTC CACGCTGGTC GGCCACGACA CCTTCACCAA
GGTGAAGCCG TCCGCCGCCT CAAGCGGAGG CGGTGGATCA GGTGGAGGCC
ATCATCACCA TCACCATGAA TTCTAATAGC TCGAG
```

FIG. 18D

Human SA-IL-2 Protein Sequence (SEQ ID NO : 9)

```
RSAPTSSSTKKTQLQLEHLLLDLQMILNGINNYKNPKLTRMLTFKFYMPKKATELKHLQCLEEE
LKPLKEVLNLAQSKNFHLRPRDLISNINVIVLELKGSETTFMCEYADETATIVEFLNRWITFSQ
SIISTLTAEAAAKEAAAKAAAGTITGTWYNQLGSTFIVTAGADGALTGTYESAVGNAESRYVLT
GRYDSAPATDGSGTALGWTVAWKNNYRNAHSATTWSGQYVGGAEARINTQWLLTSGATEANAWK
STLVGHDTFTKVKPSAASSGGGGSGGGHHHHHHEF FE
```

SA=124AA, IL-2=133AA.

IL-2-SA construct=293 aa, which translates to 31.88 kDa.

ND FOREIGN

SEQUENCE LISTING

<160> NUMBER OF SEQ ID NOS: 11

<210> SEQ ID NO 1

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Gly Ser Gly Gly Gly Ser Gly
1               5                   10

<210> SEQ ID NO 2
<211> LENGTH: 912
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
agatctgatt acaaggatga cgatgacaag ggtaccatca ccggcacctg gtacaaccag      60
ctcggctcga ccttcatcgt gaccgcgggc gccgatggcg ccctgaccgg aacctacgag     120
tcggccgtcg gcaacgccga gagccgctac gtcctgaccg gtcgttacga cagcgccccg     180
gccaccgacg gcagcggcac cgccctcggt tggacggtgg cctggaagaa taactaccgc     240
aacgcccact ccgcgaccac gtggagcggc cagtacgtcg gcggcgccga ggcgaggatc     300
aacacccagt ggctgttgac ctccggcgcc accgaggcca cgcctggaa gtccacgctg      360 gtcggccacg acaccttcac caaggtgaag ccgtccgccg cctcaagcgg aggaggagga     420
tcaggaggag gaggatcagg agaattcata ggccaccccca gtccaccccc tgaaaaaaag    480
gagctgagga agtggcccca tttaacaggc aagtccaact caaggtccat gcctctggaa     540
tgggaagaca cctatggaat tgtcctgctt tctggagtga agtataagaa gggtggcctt     600
gtgatcaatg aaactgggct gtactttgta tattccaaag tatacttccg gggtcaatct     660
tgcaacaacc tgcccctgag ccacaaggtc tacatgagga actctaagta tccccaggat     720
ctggtgatga tggagggggaa gatgatgagc tactgcacta ctgggcagat gtgggcccgc    780
agcagctacc tgggggcagt gttcaatctt accagtgctg atcatttata tgtcaacgta     840
tctgagctct ctctggtcaa ttttgaggaa tctcagacgt ttttcggctt atataagctt     900
taatagctcg ag                                                          912

<210> SEQ ID NO 3
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Arg Ser Asp Tyr Lys Asp Asp Asp Lys Gly Thr Ile Thr Gly Thr
1               5                   10                  15

Trp Tyr Asn Gln Leu Gly Ser Thr Phe Ile Val Thr Ala Gly Ala Asp
                20                  25                  30

Gly Ala Leu Thr Gly Thr Tyr Glu Ser Ala Val Gly Asn Ala Glu Ser
            35                  40                  45

Arg Tyr Val Leu Thr Gly Arg Tyr Asp Ser Ala Pro Ala Thr Asp Gly
        50                  55                  60

Ser Gly Thr Ala Leu Gly Trp Thr Val Ala Trp Lys Asn Asn Tyr Arg
```

```
                65                  70                  75                  80
Asn Ala His Ser Ala Thr Thr Trp Ser Gly Gln Tyr Val Gly Gly Ala
                    85                  90                  95

Glu Ala Arg Ile Asn Thr Gln Trp Leu Leu Thr Ser Gly Ala Thr Glu
            100                 105                 110

Ala Asn Ala Trp Lys Ser Thr Leu Val Gly His Asp Thr Phe Thr Lys
        115                 120                 125

Val Lys Pro Ser Ala Ala Ser Ser Gly Gly Gly Ser Gly Gly Gly
    130                 135                 140

Gly Ser Gly Glu Phe Ile Gly His Pro Ser Pro Pro Glu Lys Lys
145                 150                 155                 160

Glu Leu Arg Lys Val Ala His Leu Thr Gly Lys Ser Asn Ser Arg Ser
                165                 170                 175

Met Pro Leu Glu Trp Glu Asp Thr Tyr Gly Ile Val Leu Leu Ser Gly
            180                 185                 190

Val Lys Tyr Lys Lys Gly Gly Leu Val Ile Asn Glu Thr Gly Leu Tyr
        195                 200                 205

Phe Val Tyr Ser Lys Val Tyr Phe Arg Gly Gln Ser Cys Asn Asn Leu
    210                 215                 220

Pro Leu Ser His Lys Val Tyr Met Arg Asn Ser Lys Tyr Pro Gln Asp
225                 230                 235                 240

Leu Val Met Met Glu Gly Lys Met Met Ser Tyr Cys Thr Thr Gly Gln
                245                 250                 255

Met Trp Ala Arg Ser Ser Tyr Leu Gly Ala Val Phe Asn Leu Thr Ser
            260                 265                 270

Ala Asp His Leu Tyr Val Asn Val Ser Glu Leu Ser Leu Val Asn Phe
        275                 280                 285

Glu Glu Ser Gln Thr Phe Phe Gly Leu Tyr Lys Leu
    290                 295                 300

<210> SEQ ID NO 4
<211> LENGTH: 6012
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccag tgaattttaa cgttgcagga    420
caggatgtgg tgcccgatgt gactagctct ttgctgcagg ccgtcctatc ctctggttcc    480
gataagagac ccagaactcc ggcccccccac cgcccaccgc cacccccata catatgtggt    540
acgcaagtaa gagtgcctgc gcatgcccca tgtgccccac caagagtttt gcatcccata    600
caagtcccca aagtggagaa ccgaaccaat tcttcgcggg cagaacaaaa gcttctgcac    660
acgtctccac tcgaatttgg agccggccgg cgtgtgcaaa agaggtgaat cgaacgaaag    720
```

```
acccgtgtgt aaagccgcgt ttccaaaatg tataaaaccg agagcatctg gccaatgtgc    780
atcagttgtg gtcagcagca aaatcaagtg aatcatctca gtgcaactaa agggggatc    840
cgatctcaat atgaagttat gcatattact ggccgtcgtg gcctttgttg gcctctcgct    900
cgggagatct gattacaagg atgacgatga caagggtacc atcaccggca cctggtacaa    960
ccagctcggc tcgaccttca tcgtgaccgc gggcgccgat ggcgccctga ccggaaccta   1020
cgagtcggcc gtcggcaacg ccgagagccg ctacgtcctg accggtcgtt acgacagcgc   1080
cccggccacc gacggcagcg gcaccgccct cggttggacg gtggcctgga agaataacta   1140
ccgcaacgcc cactccgcga ccacgtggag cggccagtac gtcggcggcg ccgaggcgag   1200
gatcaacacc cagtggctgt tgacctccgg cgccaccgag gccaacgcct ggaagtccac   1260
gctggtcggc cacgacacct tcaccaaggt gaagccgtcc gccgcctcaa gcggaggagg   1320
aggatcagga ggaggaggat caggagaatt catagccaac cccagcacac cctctgaaac   1380
caaaaagcca aggagtgtgg cccacttaac agggaacccc cgctcaaggt ccatccctct   1440
ggaatgggaa gacacatatg gaactgcttt gatctctgga gtgaagtata agaaaggcgg   1500
ccttgtgatc aatgaggctg ggttgtactt cgtatattcc aaagtatact tccggggtca   1560
gtcttgcaac agccagcccc taagcccacaa ggtctatatg aggaacttta agtatcctgg   1620
ggatctggtg ctaatggagg agaagaagtt gaattactgc actactggcc agatatgggc   1680
ccacagcagc tacctagggg cagtatttaa tcttaccgtt gctgaccatt tatatgtcaa   1740
catatctcaa ctctctctga tcaatttttga ggaatctaag accttttttg gcttatataa   1800
gctttaactc gagtctagag ggcccttcga aggtaagcct atccctaacc ctctcctcgg   1860
tctcgattct acgcgtaccg gtcatcatca ccatcaccat tgagtttaaa cccgctgatc   1920
agcctcgact gtgccttcta aggctgagc tcgctgatca gcctcgatcg aggatccaga   1980
catgataaga tacattgatg agtttggaca aaccacaact agaatgcagt gaaaaaaatg   2040
cttttatttgt gaaatttgtg atgctattgc tttatttgta accattataa gctgcaataa   2100
acaagttaac aacaacaatt gctaaaatac agcatagcaa aactttaacc tccaaatcaa   2160
gcctctactt gaatccttttt ctgagggatg aataaggcat aggcatcagg ggctgttgcc   2220
aatgtgcatt agctgtttgc agcctcacct tctttcatgg agtttaagat atagtgtatt   2280
ttcccaaggt ttgaactagc tcttcatttc tttatgtttt aaatgcactg acctcccaca   2340
ttccctttttt agtaaaatat tcagaaataa tttaaataca tcattgcaat gaaaataaat   2400
gttttttatt aggcagaatc cagatgctca aggcccttca taatatcccc cagtttagta   2460
gttggactta gggaacaaag gaacctttaa tagaaattgg acagcaagaa agcgagcttc   2520
tagctcaggt ttaagctcca ggcttccttg tcatgcacca agttcttggg ccttctggaa   2580
cctcaacatc agctgtcaca gtgaatccca gtctttcata aaaaggcagg tttctgggag   2640
cagaagtttc cagaaaggca ggaactccag ccctttcagc agcttcaact ccaggcagaa   2700
caacagcaga tcccagaccc tttccctggt ggtcagggct cactccaaca gttgccagaa   2760
accaagctgg ctcttttggc ctgtgtggtg ccagcagacc ttccatttgt tgttgtgctg   2820
ccagcctgct tccagagagc tcagccattc ttggtccaat ttcagcaaaa acagcaccag   2880
cttcaacaga ctcaggtgtt gtccaaactg caacagcagc tccatcatct gcaacccaaa   2940
cttttccaat gtccagtccc actctggtga ggaagagttc ttgcagttct gtcaccctct   3000
caatgtgcct gtcagggtca actgtgtgcc ttgttcaggg gtagtctgca aaagcagcag   3060
ccagtgttct cacagctctt ggaacatcat ctctggttgc cagcctcact gtgggtttgt   3120
```

```
actcagtcat ggtggccctc ctatagtgag tcgtattata ctatgccgat atactatgcc   3180
gatgattaat tgtcaaaaca gcgtggatgg cgtctccagc ttatctgacg gttcactaaa   3240
cgagctctgc ttatatagac ctcccaccgt acacgcctac cgcccatttg cgtcaatggg   3300
gcggagttgt tacgacattt tggaaagtcc cgttgattta ctagtcaaaa caaactccca   3360
ttgacgtcaa tggggtggag acttggaaat ccccgtgagt caaaccgcta tccacgccca   3420
ttgatgtact gccaaaaccg catcatcatg gtaatagcga tgactaatac gtagatgtac   3480
tgccaagtag gaaagtccca taaggtcatg tactgggcat aatgccaggc gggccattta   3540
ccgtcattga cgtcaatagg gggcgtactt ggcatatgat acacttgatg tactgccaag   3600
tgggcagttt accgtaaata ctccacccat tgacgtcaat ggaaagtccc tattggcgtt   3660
actatgggaa catacgtcat tattgacgtc aatgggcggg ggtcgttggg cggtcagcca   3720
ggcgggccat ttaccgtaag ttatgtaacg cctgcgtcga cctgcaggca tgcaagcttg   3780
gcgtaatcat ggtcatagct gtttcctgtg tgaaattgtt atccgctcac aattccacac   3840
aacatacgag ccggaagcat aaagtgtaaa gcctggggtg cctaatgagt gagctaactc   3900
acattaattg cgttgcgctc actgcccgct ttccagtcgg gaaacctgtc gtgccagctg   3960
cattaatgaa tcggccaacg cgcggggaga ggcggtttgc gtattgggcg ctcttccgct   4020
tcctcgctca ctgactcgct gcgctcggtc gttcggctgc ggcgagcggt atcagctcac   4080
tcaaaggcgg taatacggtt atccacagaa tcaggggata acgcaggaaa gaacatgtga   4140
gcaaaaggcc agcaaaaggc caggaaccgt aaaaaggccg cgttgctggc gtttttccat   4200
aggctccgcc cccctgacga gcatcacaaa aatcgacgct caagtcagag gtggcgaaac   4260
ccgacaggac tataaagata ccaggcgttt ccccctggaa gctccctcgt gcgctctcct   4320
gttccgaccc tgccgcttac cggatacctg tccgcctttc tcccttcggg aagcgtggcg   4380
ctttctcata gctcacgctg taggtatctc agttcggtgt aggtcgttcg ctccaagctg   4440
ggctgtgtgc acgaaccccc cgttcagccc gaccgctgcg ccttatccgg taactatcgt   4500
cttgagtcca acccggtaag acacgactta tcgccactgg cagcagccac tggtaacagg   4560
attagcagag cgaggtatgt aggcggtgct acagagttct tgaagtggtg gcctaactac   4620
ggctacacta aaggacagt atttggtatc tgcgctctgc tgaagccagt taccttcgga   4680
aaaagagttg gtagctcttg atccggcaaa caaaccaccg ctggtagcgg tggtttttt   4740
gtttgcaagc agcagattac gcgcagaaaa aaaggatctc aagaagatcc tttgatcttt   4800
tctacggggt ctgacgctca gtggaacgaa aactcacgtt aagggatttt ggtcatgaga   4860
ttatcaaaaa ggatcttcac ctagatcctt ttaaattaaa aatgaagttt taaatcaatc   4920
taaagtatat atgagtaaac ttggtctgac agttaccaat gcttaatcag tgaggcacct   4980
atctcagcga tctgtctatt tcgttcatcc atagttgcct gactccccgt cgtgtagata   5040
actacgatac gggagggctt accatctggc cccagtgctg caatgatacc gcgagaccca   5100
cgctcaccgg ctccagattt atcagcaata aaccagccag ccggaagggc cgagcgcaga   5160
agtggtcctg caactttatc cgcctccatc cagtctatta attgttgccg ggaagctaga   5220
gtaagtagtt cgccagttaa tagtttgcgc aacgttgttg ccattgctac aggcatcgtg   5280
gtgtcacgct cgtcgtttgg tatggcttca ttcagctccg gttcccaacg atcaaggcga   5340
gttacatgat cccccatgtt gtgcaaaaaa gcggttagct ccttcggtcc tccgatcgtt   5400
gtcagaagta agttggccgc agtgttatca ctcatggtta tggcagcact gcataattct   5460
```

-continued

```
cttactgtca tgccatccgt aagatgcttt tctgtgactg gtgagtactc aaccaagtca    5520
ttctgagaat agtgtatgcg gcgaccgagt tgctcttgcc cggcgtcaat acgggataat    5580
accgcgccac atagcagaac tttaaaagtg ctcatcattg gaaaacgttc ttcggggcga    5640
aaactctcaa ggatcttacc gctgttgaga tccagttcga tgtaacccac tcgtgcaccc    5700
aactgatctt cagcatcttt tactttcacc agcgtttctg ggtgagcaaa acaggaagg    5760 caaaatgccg caaaaaggg aataagggcg acacggaaat gttgaatact catactcttc    5820 cttttcaat attattgaag catttatcag ggttattgtc tcatgagcgg atacatattt    5880
gaatgtattt agaaaaataa acaaataggg gttccgcgca catttccccg aaaagtgcca    5940
cctgacgtct aagaaaccat tattatcatg acattaacct ataaaaatag gcgtatcacg    6000
aggccctttc gt                                                       6012
```

<210> SEQ ID NO 5
<211> LENGTH: 300
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Arg Ser Asp Tyr Lys Asp Asp Asp Lys Gly Thr Ile Thr Gly Thr
 1               5                  10                  15

Trp Tyr Asn Gln Leu Gly Ser Thr Phe Ile Val Thr Ala Gly Ala Asp
                20                  25                  30

Gly Ala Leu Thr Gly Thr Tyr Glu Ser Ala Val Gly Asn Ala Glu Ser
            35                  40                  45

Arg Tyr Val Leu Thr Gly Arg Tyr Asp Ser Ala Pro Ala Thr Asp Gly
        50                  55                  60

Ser Gly Thr Ala Leu Gly Trp Thr Val Ala Trp Lys Asn Asn Tyr Arg
 65                  70                  75                  80

Asn Ala His Ser Ala Thr Thr Trp Ser Gly Gln Tyr Val Gly Gly Ala
                 85                  90                  95

Glu Ala Arg Ile Asn Thr Gln Trp Leu Leu Thr Ser Gly Ala Thr Glu
            100                 105                 110

Ala Asn Ala Trp Lys Ser Thr Leu Val Gly His Asp Thr Phe Thr Lys
        115                 120                 125

Val Lys Pro Ser Ala Ala Ser Ser Gly Gly Gly Ser Gly Gly Gly
    130                 135                 140

Gly Ser Gly Glu Phe Ile Ala Asn Pro Ser Pro Ser Glu Thr Lys
145                 150                 155                 160

Lys Pro Arg Ser Val Ala His Leu Thr Gly Asn Pro Arg Ser Arg Ser
                165                 170                 175

Ile Pro Leu Glu Trp Glu Asp Thr Tyr Gly Thr Ala Leu Ile Ser Gly
            180                 185                 190

Val Lys Tyr Lys Lys Gly Gly Leu Val Ile Asn Glu Ala Gly Leu Tyr
        195                 200                 205

Phe Val Tyr Ser Lys Val Tyr Phe Arg Gly Gln Ser Cys Asn Ser Gln
    210                 215                 220

Pro Leu Ser His Lys Val Tyr Met Arg Asn Phe Lys Tyr Pro Gly Asp
225                 230                 235                 240

Leu Val Leu Met Glu Glu Lys Lys Leu Asn Tyr Cys Thr Thr Gly Gln
                245                 250                 255
```

```
Ile Trp Ala His Ser Ser Tyr Leu Gly Ala Val Phe Asn Leu Thr Val
            260                 265                 270

Ala Asp His Leu Tyr Val Asn Ile Ser Gln Leu Ser Leu Ile Asn Phe
        275                 280                 285

Glu Glu Ser Lys Thr Phe Phe Gly Leu Tyr Lys Leu
    290                 295                 300

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Glu Ala Ala Ala Lys Glu Ala Ala Ala Lys Ala Ala Ala
1               5                   10

<210> SEQ ID NO 7
<211> LENGTH: 879
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
agatctgcac ctacttcaag ttctacaaag aaaacacagc tacaactgga gcatttactg      60
ctggatttac agatgatttt gaatggaatt aataattaca agaatcccaa actcaccagg     120
atgctcacat ttaagtttta catgcccaag aaggccacag aactgaaaca tcttcagtgt     180
ctagaagaag aactcaaacc tctgaaggaa gtgctaaatt tagctcaaag caaaaacttt     240
cacttaagac ccagggactt aatcagcaat atcaacgtaa tagttctgga actaaaggga     300
tctgaaacaa cattcatgtg tgaatatgct gatgagacag caaccattgt agaatttctg     360
aacagatgga ttaccttttc tcaaagcatc atctcaacac taactgctga agctgcagct     420
aaagaagctg cagctaaagc tgctgctggt accatcaccg gcacctggta caaccagctc     480
ggctcgacct tcatcgtgac cgcgggcgcc gatggcgccc tgaccggaac ctacgagtcg     540
gccgtcggca acgccgagag ccgctacgtc ctgaccggtc gttacgacag cgccccggcc     600
accgacggca gcggcaccgc cctcggttgg acggtggcct ggaagaataa ctaccgcaac     660
gcccactccg cgaccacgtg gagcggccag tacgtcggcg gcgccgaggc gaggatcaac     720
acccagtggc tgttgacctc cggcgccacc gaggccaacg cctggaagtc cacgctggtc     780
ggccacgaca ccttccaccaa ggtgaagccg tccgccgcct caagcggagg cggtggatca     840
ggtggaggcc atcatcacca tcaccatgaa ttcctcgag                            879

<210> SEQ ID NO 8
<211> LENGTH: 885
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
agatctgcac ctacttcaag ttctacaaag aaaacacagc tacaactgga gcatttactg      60
ctggatttac agatgatttt gaatggaatt aataattaca agaatcccaa actcaccagg     120
```

-continued

```
atgctcacat ttaagtttta catgcccaag aaggccacag aactgaaaca tcttcagtgt    180
ctagaagaag aactcaaacc tctgaaggaa gtgctaaatt tagctcaaag caaaaacttt    240
cacttaagac ccagggactt aatcagcaat atcaacgtaa tagttctgga actaaaggga    300
tctgaaacaa cattcatgtg tgaatatgct gatgagacag caaccattgt agaatttctg    360
aacagatgga ttacctttc tcaaagcatc atctcaacac taactgctga agctgcagct    420
aaagaagctg cagctaaagc tgctgctggt accataccg gcacctggta caaccagctc    480
ggctcgacct tcatcgtgac cgcgggcgcc gatggcgccc tgaccggaac ctacgagtcg    540
gccgtcggca cgccgagag ccgctacgtc ctgaccggtc gttacgacag cgccccggcc    600
accgacggca gcggcaccgc cctcggttgg acggtggcct ggaagaataa ctaccgcaac    660
gcccactccg cgaccacgtg gagcggccag tacgtcggcg cgccgaggc gaggatcaac    720 acccagtggc tgttgacctc cggcgccacc gaggccaacg cctggaagtc cacgctggtc    780
ggccacgaca ccttcaccaa ggtgaagccg tccgccgcct caagcggagg cggtggatca    840
ggtggaggcc atcatcacca tcaccatgaa ttctaatagc tcgag                    885
```

<210> SEQ ID NO 9
<211> LENGTH: 293
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Arg Ser Ala Pro Thr Ser Ser Thr Lys Lys Thr Gln Leu Gln Leu
1               5                   10                  15

Glu His Leu Leu Leu Asp Leu Gln Met Ile Leu Asn Gly Ile Asn Asn
                20                  25                  30

Tyr Lys Asn Pro Lys Leu Thr Arg Met Leu Thr Phe Lys Phe Tyr Met
            35                  40                  45

Pro Lys Lys Ala Thr Glu Leu Lys His Leu Gln Cys Leu Glu Glu Glu
        50                  55                  60

Leu Lys Pro Leu Lys Glu Val Leu Asn Leu Ala Gln Ser Lys Asn Phe
65                  70                  75                  80

His Leu Arg Pro Arg Asp Leu Ile Ser Asn Ile Asn Val Ile Val Leu
                85                  90                  95

Glu Leu Lys Gly Ser Glu Thr Thr Phe Met Cys Glu Tyr Ala Asp Glu
            100                 105                 110

Thr Ala Thr Ile Val Glu Phe Leu Asn Arg Trp Ile Thr Phe Ser Gln
        115                 120                 125

Ser Ile Ile Ser Thr Leu Thr Ala Glu Ala Ala Ala Lys Glu Ala Ala
    130                 135                 140

Ala Lys Ala Ala Ala Gly Thr Ile Thr Gly Thr Trp Tyr Asn Gln Leu
145                 150                 155                 160

Gly Ser Thr Phe Ile Val Thr Ala Gly Ala Asp Gly Ala Leu Thr Gly
                165                 170                 175

Thr Tyr Glu Ser Ala Val Gly Asn Ala Glu Ser Arg Tyr Val Leu Thr
            180                 185                 190

Gly Arg Tyr Asp Ser Ala Pro Ala Thr Asp Gly Ser Gly Thr Ala Leu
        195                 200                 205

Gly Trp Thr Val Ala Trp Lys Asn Asn Tyr Arg Asn Ala His Ser Ala
    210                 215                 220
```

```
-continued

Thr Thr Trp Ser Gly Gln Tyr Val Gly Gly Ala Glu Ala Arg Ile Asn
225                 230                 235                 240

Thr Gln Trp Leu Leu Thr Ser Gly Ala Thr Glu Ala Asn Ala Trp Lys
                245                 250                 255

Ser Thr Leu Val Gly His Asp Thr Phe Thr Lys Val Lys Pro Ser Ala
                260                 265                 270

Ala Ser Ser Gly Gly Gly Ser Gly Gly Gly His His His His
        275                 280                 285

His Glu Phe Phe Glu
    290

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Ser Gly Gly Gly Thr
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 11

His His His His His His
1               5
```

IMMUNOMODULATION FOR THE LONG TERM PREVENTION AND TREATMENT OF AUTOIMMUNE DISEASES AND FOREIGN TISSUE REJECTION

CROSS REFERENCE TO RELATED APPLICATIONS

This application is the U.S. National Stage of International Application PCT/US2016/038185, filed Jun. 17, 2016, which claims priority to U.S. Provisional Patent Application No. 62/181,815, filed Jun. 19, 2015, each of which is incorporated herein by reference in its entirety.

GOVERNMENT GRANT SUPPORT CLAUSE

This invention was made with U.S. Federal support under Grant Award No. T32A 1055456 awarded by the National Institute for Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 22, 2018, is named 089885-0153_SL.txt and is 21,494 bytes in size.

TECHNICAL FIELD

Described herein are pharmaceutical compositions and methods for modulating the immune system, such as for the prevention and treatment of autoimmune diseases and foreign graft rejection.

BACKGROUND

Autoimmune diseases and graft rejection are well recognized problems. Current clinical practice is to administer immunosuppressants that prevent T-cell activity. Such immunosuppressants are administered for an extended period in autoimmune disease, and often for the lifetime of the patient who has received foreign grafts. The requirement for long term use of immunosuppressants makes successful treatment dependent on frequent medical monitoring, and exposes the patient to serious side effects from the drugs. As an alternative, it would be advantageous to develop a treatment that "teaches" the immune system to control/eliminate destructive immune responses generated by specific antigens.

The present inventor has previously demonstrated immunomodulation by display of SA-FasL on the surface of biological membranes modified with biotin. Injecting subjects with foreign cells decorated with SA-FasL has shown efficacy in modulating immune responses and achieving long term survival of tolerance to grafted tissues. Nevertheless, there remains a need for methods that "teach" the immune system to tolerate specific foreign and self antigens, that exhibit improved efficacy and are useful in a broad variety of applications.

SUMMARY

The invention described herein relates to the surprising discovery that soluble SA-FasL, optionally together with IL-2, optionally together with FasL-decorated cells and/or IL-2-decorated cells, is useful in methods for inducing long-term and specific immunosuppression. Thus, described herein are compositions, medicaments and methods useful for immunomodulation, such as for long-term prevention and/or treatment of autoimmune diseases and long-term prevention and/or treatment of graft rejection.

In accordance with some embodiments, there are provided medicaments for use in inducing immune tolerance in a subject in need thereof, comprising (i) a chimeric FasL protein comprising a FasL moiety and a streptavidin or avidin moiety and (ii) an IL-2 protein. In accordance with any embodiments, the chimeric FasL protein and IL-2 protein may be provided in separate compositions or in the same composition.

The chimeric FasL protein may be selected from soluble chimeric FasL proteins comprising a FasL moiety and a streptavidin or avidin moiety, and chimeric FasL-decorated cells comprising a chimeric FasL protein comprising a FasL moiety and a streptavidin or avidin moiety bound to a cell surface via a biotin moiety on the cell surface. One embodiment of a chimeric FasL protein has the amino acid sequence of SEQ ID NO: 3.

The IL-2 protein may be selected from soluble IL-2 proteins, soluble chimeric IL-2 proteins comprising an IL-2 moiety and a streptavidin or avidin moiety, and chimeric IL-2-decorated cells comprising a chimeric IL-2 protein comprising an IL-2 moiety and a streptavidin or avidin moiety bound to a cell surface via a biotin moiety on the cell surface. One embodiment of a chimeric IL-2 protein has the amino acid sequence of SEQ ID NO: 9.

In one embodiment, the medicament comprises soluble chimeric FasL protein and soluble IL-2 protein or soluble chimeric IL-2 protein. In another embodiment, the medicament comprises chimeric FasL-decorated cells and soluble IL-2 protein or soluble chimeric IL-2 protein. In another, the medicament comprises soluble chimeric FasL protein and chimeric IL-2-decorated cells. In another, the medicament comprises chimeric FasL-decorated cells and chimeric IL-2-decorated cells. In specific embodiments, a medicament for use in inducing immune tolerance may comprise soluble chimeric FasL protein comprising a FasL moiety and a streptavidin or avidin moiety.

The medicaments are effective to induce immunomodulation in subjects in need of such immunomodulation. For example, a subject may be in in need of treatment for type 1 diabetes and the decorated cells, if present, may be islet cells, splenocytes, PBMC, bone marrow cells, mesenchymal stem cells, hematopoietic stem cells, stem cells, or induced pluripotent stem cells. Alternatively, the subject may be in need of the treatment or prevention of allograft rejection and the decorated cells, if present, may be cells from the allograft donor, such as cells selected from the group consisting of allograft bone marrow cells, allograft cardiac myocytes and allograft vascular cells, or other cells from the allograft donor.

The invention also includes methods for inducing immunomodulation. In accordance with some embodiments, there are provided methods of inducing immune tolerance in a subject in need thereof comprising administering to the individual (i) a chimeric FasL protein comprising a FasL moiety and a streptavidin or avidin moiety and (ii) an IL-2 protein. In accordance with any embodiments, the chimeric FasL protein and IL-2 protein may be administered together, or separately, in any order.

The chimeric FasL protein may be selected from soluble chimeric FasL proteins comprising a FasL moiety and a streptavidin or avidin moiety and chimeric FasL-decorated cells comprising a chimeric FasL protein comprising a FasL moiety and a streptavidin or avidin moiety bound to a cell surface via a biotin moiety on the cell surface. One embodiment of a chimeric FasL protein has the amino acid sequence of SEQ ID NO: 3.

The IL-2 protein may be selected from the group consisting of soluble IL-2 proteins, soluble chimeric IL-2 proteins comprising an IL-2 moiety and a streptavidin or avidin moiety; and chimeric IL-2-decorated cells comprising a chimeric IL-2 protein comprising an IL-2 moiety and a streptavidin or avidin moiety bound to a cell surface via a biotin moiety on the cell surface. One embodiment of a chimeric IL-2 protein has the amino acid sequence of SEQ ID NO: 9.

The methods may be used to induce immunomodulation in subjects in need of such immunomodulation. For example, a subject may be in need of treatment for type 1 diabetes and the decorated cells, if present, may be islet cells, PBMCs or splenocytes, bone marrow cells, mesenchymal stem cells, hematopoietic stem cells, stem cells, or induced pluripotent stem cells. In some embodiments, such a method may comprise administering to the subject in need thereof:

(a) chimeric FasL-decorated pancreatic islet cells;
(b)(i) soluble chimeric FasL protein and (ii) soluble IL-2 protein or soluble chimeric IL-2 protein, in amounts effective to induce immune tolerance to pancreatic islet cells; and
(c) optionally, administering an immunosuppressant, such as rapamycin or cyclophosamide.

In further embodiments, a subject is in need of the treatment or prevention of allograft rejection and the decorated cells, if present, are cells of the allograft, such as cells selected from the group consisting of allograft bone marrow cells, PBMC, mesenchymal stem cells, hematopoietic stem cells, stem cells, induced pluripotent stem cells, cardiac myocytes and vascular cells. In some embodiments, such a method of treating or preventing allograft rejection in a subject in need thereof, comprises (a) chimeric FasL-decorated cells from the allograft donor, such as cells selected from the group consisting of allograft bone marrow cells, allograft cardiac myocytes and allograft vascular cells, or other cells from the allograft donor; (b) administering (i) soluble chimeric FasL protein and (ii) soluble IL-2 protein or soluble chimeric IL-2 protein, in amounts effective to induce immune tolerance to the allograft cells; and optionally, administering an immunosuppressant, such as rapamycin or cyclophosamide. The cells from the allograft donor may also be decorated with one or both of FasL and IL-2.

In accordance with further embodiments, there are provided methods of treating or preventing autoimmunity in a subject in need thereof, comprising (a) administering to the subject cells decorated with chimeric FasL and optionally decorated with chimeric IL-2, and (b) administering (i) soluble chimeric FasL protein and (ii) soluble IL-2 protein or soluble chimeric IL-2 protein, in amounts effective to induce immune tolerance to the autoantigen; wherein the cells are selected from (i) a cell expressing an autoantigen (ii) a cell decorated with an autoantigen and (iii) a dendritic cell pulsed with the autoantigen. In particular embodiments, the cell expressing an autoantigen or the cell decorated with the autoantigen is obtained from the subject. In specific embodiments, the cell is selected from bone marrow cells, dendritic cells, PBMC, hematopoietic stem cells, and mesenchymal stem cells, including any of such cells obtained from the subject.

In accordance with further embodiments, there are provided methods of treating or preventing autoimmunity in a subject in need thereof, comprising (a) administering an autoantigen presented on a cell selected from the group consisting of (i) a cell expressing the autoantigen (ii) a cell decorated with the autoantigen and (iii) a dendritic cell pulsed with the autoantigen, wherein the cell optionally is decorated with chimeric FasL and/or chimeric IL-2, and (b) administering (i) soluble chimeric FasL protein and (ii) soluble IL-2 protein or soluble chimeric IL-2 protein, in amounts effective to induce immune tolerance to the autoantigen. In particular embodiments, the cell is obtained from the subject. In specific embodiments, the cell is selected from bone marrow cells, dendritic cells, PBMC, hematopoietic stem cells, and mesenchymal stem cells, including any of such cells obtained from the subject.

BRIEF DESCRIPTION OF THE DRAWINGS

(FIG. 11A) average donor chimerism, (FIG. 11B) percent engraftment, (FIG. 11C) Long-term chimeric mice reject C3H third-party, but not BALB/c donor skin, demonstrating donor-specific tolerance.

(FIG. 12A) average donor chimerism, (FIG. 12B) percent engraftment, (FIG. 12C) long-term chimeric mice reject C3H third-party, but not BALB/c donor skin, demonstrating donor-specific tolerance.

FIG. 13A-E. Mice develop long-term multilineage donor chimerism. Various tissues were harvested from mice with long-term donor mixed chimerism that was established through complete treatment with mFasL/IL-2-BMC+CYP (d+2)+sFasL+sIL-2+Rapa, as in FIG. 12. The tissues were, processed into single cell suspension, stained with antibodies to the indicated cell surface markers, and analyzed using flow cytometry. FIG. 13A shows total percentage of donor cells in the indicated tissues; FIG. 13B, donor cell type as a percentage of total donor cells in peripheral blood lymphocytes; FIG. 13C, donor cell type as a percentage of total donor cells in spleen, FIG. 13D, donor cell type as a percentage of total donor cells in bone marrow; FIG. 13E, donor cell type as a percentage of total donor cells in thymus. Total donor chimerism.

FIG. 14A-D. Mice with long-term donor mixed chimerism generate in vitro response to third party, but not donor alloantigens. Spleens were harvested from long-term (>100 days) durable mixed chimeras and control mice that rejected donor BMCs shown in FIG. 12. Spleens were processed into single cell suspension, labeled with 2.5 μM CF SE, resuspended in DMEM, and $50\times10^6$ CFSE labeled splenocytes were plated on a petri dish for 45 minutes at 37° C. to enrich lymphocytes. After 45 minutes non-adherent cells were collected, washed, and incubated ($1\times10^5$ cells) with irradiated (2000 cGy; $1\times10^5$ cells) donor BALB/c or C3H splenocytes as stimulators in 96-well U-bottom titer plates in mixed lymphocyte reaction medium. Irradiated syngeneic C57BL/6 cells were used as controls. After 4 days, cells were stained with fluorochrome-labeled antibodies against rat CD4 and CD8, analyzed by flow cytometry gating on live cells, and the percentage of proliferating cells were graphed. FIG. 14A shows that CD4+ T cells from nonchimeric mice respond to irradiated splenocytes from both donor (BLAB/c) and third party (C3H) as stimulators. FIG. 14B shows that CD4+ T cells from long-term chimeric mice respond to irradiated splenocytes from third party (C3H), but not donor (BLAB/c) as stimulators. FIG. 14C shows that CD8+ T cells from nonchimeric mice respond to irradiated splenocytes from both donor (BLAB/c) and third party (C3H) as stimulators. FIG. 14D shows that CD8+ T cells from long-term chimeric mice respond to irradiated splenocytes from third party (C3H), but not donor (BLAB/c) as stimulators.

FIG. 15. FIG. 15 sets forth the human SA-FasL nucleotide construct and the linker sequence (SEQ ID NO:1) between the streptavidin and FasL sequences.

FIG. 16A-B. FIGS. 16A and 16B set forth the human SA-FasL nucleotide sequence (SEQ ID NO:2) and protein sequence (SEQ ID NO: 3), respectively, of a fusion protein comprising streptavidin and FasL.

FIG. 17A-B. FIGS. 17A and 17B set forth the rat SA-FasL nucleotide sequence (SEQ ID NO:4) and protein sequence (SEQ ID NO: 5), respectively, of a fusion protein comprising streptavidin and FasL.

FIG. 18A-D. FIG. 15A sets forth the human SA-IL-2 Construct and linker sequences SEQ ID NO: 6 and SEQ ID NO: 10. FIGS. 18B and 18C set forth un-optimized DNA sequences SEQ ID NO: 7 and SEQ ID NO: 8, respectively. FIG. 18D sets forth human SA-IL-2 protein sequence (SEQ ID NO: 9).

DETAILED DESCRIPTION

Figure 1:
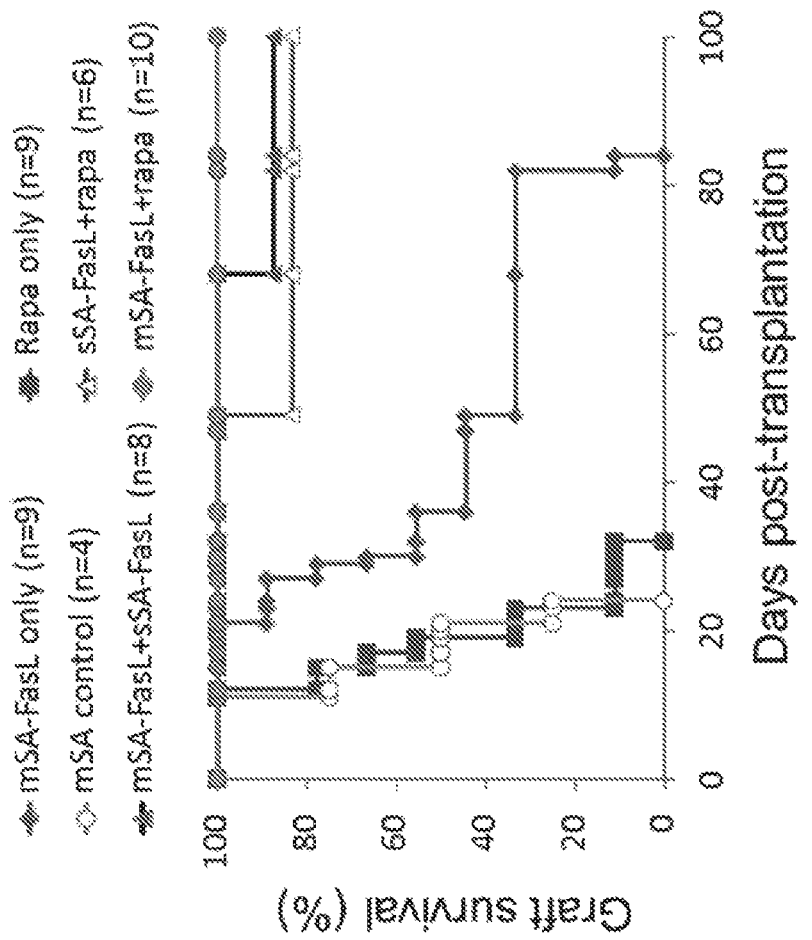
FIG. 1. Systemic immunomodulation with soluble SA-FasL synergizes with SA-FasL-engineered islets for long-term survival. BALB/c islets were engineered with SA-FasL (mSA-FasL) or SA control (mSA) proteins and transplanted under the kidney capsule of STZ diabetic C57BL/6 mice. Soluble (s)SA-FasL was administered i.p. at 2-5 µg/mouse on days 1, 3, 5, 7 post-transplantation. In selected groups rapamycin was used at 0.2 mg/kg daily for 15 days starting the day of transplantation.

The present invention relates to the discovery that soluble SA-FasL, optionally together with IL-2, optionally together with FasL-decorated cells and/or IL-2-decorated cells, can be used to achieve long-term, specific immunosuppression.

$CD8^+$ and $CD4^+$ T effector cells, in particular $CD4^+$ T cells, play a critical role in the initiation and perpetuation of various autoimmune diseases, including type I diabetes, rheumatoid arthritis, lupus, multiple sclerosis, and in foreign graft rejection, including rejection of allogeneic and xenogeneic grafts. T effector cells, therefore, represent an important target for immune modulation to prevent and treat these diseases. Under normal physiological conditions, T effector cells are kept in check by another class of T cells, designated as T regulatory cells. Mounting scientific evidence demonstrates that the disturbance of the physiological balance between T effector and T regulatory cells in favor of T effector cells is an underlying cause of many autoimmune diseases and foreign graft rejection. Approaches that target both T effector cells and T regulatory cells have significant therapeutic potential for reestablishing the physiological balance in autoimmunity, and for tilting the balance in favor of T regulatory cells in case of graft rejection.

Following antigen recognition and activation, T effector cells upregulate the Fas receptor on their surface and become sensitive to FasL-mediated apoptosis. Importantly FasL-mediated apoptosis is critical to the induction of self-tolerance and maintenance as deficiency in Fas or FasL is associated with massive autoimmunity both in humans and in rodents. This suggests that there are no compensatory mechanisms for this pathway, further emphasizing its importance as a target for immunomodulation.

Particular details of various embodiments of the invention are set forth below to illustrate certain aspects, but not to limit the scope of, the invention. It will be apparent to one of ordinary skill in the art that modifications and variations are possible without departing from the scope of the invention described herein. In the discussion that follows, specific embodiments of different aspects of the invention are described. It should be understood that any specific embodiment of one aspect may be used in conjunction with any specific embodiment of another aspect, even if every possible permutation and combination of specific embodiments is not expressly set forth.

Definitions

Unless defined otherwise, all technical and scientific terms used herein have the same meaning as commonly understood by one of ordinary skill in the art to which the presently-disclosed subject matter belongs.

For the purposes of the present application, the following terms have these definitions:

As used herein "a" or "an" means one or more, unless specifically indicated to mean only one.

"Antigen" is used herein without limitation. Antigens include proteins, lipids, sugars, nucleic acids, chemical moieties, and other moieties that induce an immune response. Antigens include proteins, which may or may not be modified, such as by glycosylation or methylation, that are cyclized or bound to lipids, for example. In many embodiments, the antigens are present on the surface of cells, such as alloantigens. An antigen may also be a self antigen. Also suitable for use as an "antigen" in accordance with the present invention are peptides comprising antigenic portions of full-length proteins, such as peptides comprising a portion of a protein that induces an immune response, such as an immunogenic epitope.

"Immune cell" as used herein includes any cell that is involved in the generation, regulation or effect of the acquired or innate immune system. Immune cells include T cells such as CD4+ cells, CD8+ cells and various other T cell subets, B cells, natural killer cells, macrophages, monocytes and dendritic cells, and neutrophils.

"Autoantigen" means a self antigen, that despite being a normal tissue constituent, is the target of a humoral or cell-mediated immune response by the host, as in autoimmune disease.

"Surface" means a cell surface, the surface of a virus, the surface of a particle (e.g., the surface of a glass particle, the surface of a polysaccharide particle, the surface of a plastic particle), the surface of a phospholipid bilayer or the surface of a solid matrix, as well as the surface of hydrogels, scaffolds, beads, and the like.

"Cell surface" has its normal meaning in the art, comprising the phospholipid bilayer of a cell membrane and the molecules directly or indirectly associated with the bilayer.

As used herein, "decorated surface" means a surface to which is bound a chimeric protein, through interaction between the chimeric protein containing one member of a binding pair (e.g. SA) and the other member of the binding pair (e.g. biotin) that is bound to the surface (e.g. a cell membrane).

"Protein" means a protein or polypeptide that is native, non-native, synthetic or modified as by covalent binding.

Other terms are defined elsewhere herein. It is to be understood that each embodiment can be operated with every other embodiment.

Proteins and Chimeric Proteins

Described herein are strategies for the induction of immune tolerance, some of which include the use of chimeric proteins which can be made by constructing chimeric cDNAs. In some embodiments, a chimeric protein comprises at least a functional portion of a member of a binding pair, such as streptavidin or avidin, operably linked to at least a functional portion of an apoptosis-inducing molecule, such as FasL, TNFa, TRAIL (Apo2 ligand), and TWEAK (Apo3 ligand) or the like. As used herein, the term "functional portion" of an apoptosis-inducing molecule means an apoptosis-inducing portion. As used herein, "FasL moiety" means at least the apoptosis-inducing moiety of FasL.

In particular embodiments, a chimeric protein comprises the extracellular domain of FasL as the apoptosis-inducing molecule, i.e. the FasL moiety. Independently, in particular embodiments, the chimeric protein comprises streptavidin (or core streptavidin) as the binding pair member. In specific embodiments, a chimeric protein comprises a streptavidin (or core streptavidin) moiety and a FasL moiety. In one embodiment, the chimeric FasL protein has the amino acid sequence of SEQ ID NO: 3.

The present invention uses IL-2. As used herein, "IL-2" includes chimeric IL-2, non chimeric IL-2 (such as may be obtained commercially) and proteins that contain the IL-2 moiety. "IL-2 moiety," as used herein contains at least the part of IL-2 sufficient for binding to the IL-2 receptor and causing signaling. In some embodiments, a chimeric protein comprises at least a functional portion of a member of a binding pair, such as streptavidin or avidin, operably linked to at least a functional portion of IL-2, i.e. IL-2 moiety. In specific embodiments, a chimeric protein comprises a streptavidin (or core streptavidin) moiety and an IL-2 moiety. In one embodiment the chimeric IL-2 protein has the amino acid sequence of SEQ ID NO: 9. It is to be understood that these constructs are representative, and not limiting of chimeric proteins that can be used accordance with the present disclosure. As an example, a cell for the production of chimeric proteins as described herein may be the *Drosophila* system that is commercially available. Those skilled in the art of producing chimeric proteins will recognize that other expression systems and vectors are suitable for production of the chimeric proteins described herein, such as *Escherichia coli*, yeast and mammalian cell cultures.

"Binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-streptavidin, biotin-avidin, hormone-receptor, receptor-ligand, enzyme-substrate, 1 gG-protein A, antigen-antibody, and the like.

An exemplary binding pair is biotin and streptavidin (SA) or avidin. As used herein "biotin" includes biotin-containing moieties that are able to bind to surfaces, such as cell surfaces (including tumor cell surfaces), such as NHS-biotin and EZ-Link™ Sulfo-NHS-LC-Biotin (Pierce). Such protein reactive forms of biotin are available commercially.

The interaction between biotin and its binding partner, avidin or streptavidin, offers several advantages in the present context. For example, biotin has an extremely high affinity for both streptavidin ($10^{13}$ $M^{-1}$) and avidin ($10^{15}$ $M^{-1}$. This embodiment also is advantageous because conjugates comprising streptavidin or avidin can be further complexed with conjugates comprising biotin. Additionally, both streptavidin and avidin are tetrameric polypeptides that each bind four molecules of biotin. Conjugates comprising streptavidin or avidin therefore have a tendency to form tetramers and higher structures, and can form complexes with multiple biotin-containing moieties.

SA or avidin fragments which retain substantial binding activity for biotin, such as at least 50% or more of the binding affinity of native SA or avidin, respectively, also may be used. Such fragments include "core streptavidin" ("CSA"), a truncated version of the full-length streptavidin polypeptide which may include streptavidin residues 13-138, 14-138, 13-139 or 14-139. See, e.g., Pahler et al., 1987, *J. Biol. Chem.*, 262: 13933-37. Other truncated forms of streptavidin and avidin that retain strong binding to biotin also may be used. See, e.g. Sano et al., 1995, *J Biol Chem.* 270(47): 28204-09 (describing core streptavidin variants 16-133 and 14-138) (U.S. Pat. No. 6,022,951). Mutants of streptavidin and core forms of strepavidin which retain substantial biotin binding activity or increased biotin binding activity also may be used. See, e.g., Chilcoti et al., 1995, *Proc Natl Acad Sci USA*. 92(5): 1754-58; Reznik et al., 1996, *Nat Biotechnol*. 14(8): 1007-11. For example, mutants with reduced immunogenicity, such as mutants mutated by site-directed mutagenesis to remove potential T cell epitopes or lymphocyte epitopes, can be used. See Meyer et al., 2001, *Protein Sci.* 10: 491-503. Likewise, mutants of avidin and core forms of avidin which retain substantial biotin binding activity or increased biotin binding activity also may be used. See Hiller et al., 1991, *J. Biochem.* 278: 573-85; Livnah et al., 1993, *Proc Natl Acad Sci USA* 90: 5076-80 (1993). For convenience, in the instant description, the terms "avidin" and "streptavidin" as used herein are intended to encompass biotin-binding fragments, mutants and core forms of these binding pair members. Avidin and streptavidin are available from commercial suppliers. Moreover, the nucleic acid sequences encoding streptavidin and avidin and the streptavidin and avidin amino acid sequences can be found, for example, in GenBank Accession Nos. X65082; X03591; NM_205320; X05343; Z21611; and Z21554.

Other mechanisms (e.g., other conjugation methods using, for example, other linking moieties or chemical or genetic cross-linking) can be used to provide linkages to bind a protein (e.g. FasL or IL-2) to a surface. Other mechanisms can be used to provide higher-order structures of immune co-stimulatory molecules, such as conjugates comprising dimers, trimers, tetramers and higher-order multimers of immune co-stimulatory molecules, which also will exhibit advantageous properties. Such conjugates are included within the scope of this invention.

As used herein, the existing of a binding moiety permits the chimeric protein to bind to e.g. a cell surface. As used herein, a cell to which is bound FasL, IL-2 and the like may be said to be "decorated" with FasL, IL-2, etc. Likewise, the FasL on a cell would be a "membrane bound FasL," "bound FasL", or "mFasL"; and the IL-2 on a cell would be "membrane bound IL-2", "bound IL-2" or "mIL-2"

A chimeric protein may also be unbound to a surface. Such a chimeric protein may be said to be "soluble." As used herein "soluble FasL" or "sFasL" means a molecule containing the FasL moiety that is not bound to a surface (such as a cell). The FasL may be a chimeric FasL. It should be noted that "soluble FasL" as used herein contains the apoptotic extracellular moiety of FasL, and is distinct from an unbound molecule derived from FasL that is unable to induce apoptosis.

A "soluble IL-2" or "sIL-2" as used herein means that the IL-2 is not bound not bound to a surface (such as a cell). The soluble IL-2 may be a chimeric IL-2, or may be non-chimeric IL-2.

Cells

Certain embodiments described herein use or comprise a cell, tissue or organ. In particular embodiments, the cell is a mammalian cell. In embodiments related to graft rejection, the cell may be of the same type as the cell of the graft to be transplanted. Additionally or alternatively, the cell may be of a different type from the graft but from the same donor, to induce tolerance to the donor graft. For example, FasL-decorated donor cells can be used to induce immune tolerance in the subject who has received, is receiving, or will receive a graft from the same donor. The administration of donor tissue, organs or cells is then more likely to be tolerated by the subject.

To illustrate, a subject may be administered pancreatic islet cells to treat diabetes. To prevent rejection, the subject may be administered pancreatic islet cells that are decorated with FasL. Additionally or alternatively, the subject may be administered a different type of FasL-decorated donor cells, such as splenocytes, PBMCs, bone marrow cells, mesenchymal stem cells, hematopoietic stem cells, stem cells, induced pluripotent stem cells, dendritic cells, cardiac myocytes, and vascular cells, etc., to induce immune tolerance to the donor's cells. Depending on the condition being treated, the subject may be administered FasL-decorated cells, such as splenocytes, PBMCs, bone marrow cells, mesenchymal stem cells, hematopoietic stem cells, stem cells, induced pluripotent stem cells, dendritic cells, cardiac myocytes, and vascular cells, etc., to treat the condition, and/or may be administered decorated or undecorated cells to treat the condition and one or more different types of FasL-decorated cells to induce immune tolerance to the donor's cells.

In some embodiments, the alloantigen is a pancreatic islet cell, a tissue, or an organ. In some embodiments, a cell used to treat the subject (or provided in the medicament) is selected from the group consisting of islet cells, bone marrow cells, hematopoietic stem cells, stem cell, induced pluripotent stem cell, human beta cell products, hepatocytes, dendritic cells, macrophages, endothelial cells, mesenchymal stem cell, and immune cells, including T cells. In further specific embodiments, the cell is part of a tissue or organ.

In some embodiments, the antigen is a self antigen. In some embodiments, a cell used to treat the subject (or provided in the medicament) is engineered to express an autoantigen, or is decorated with an autoantigen. For example, dendritic cells can be pulsed with autoantigen and thereby display the antigen on the surface.

In some embodiments, cells from the subject are used to induce immune tolerance to self that has been interrupted in autoimmune disease. That is, the "donor" and "recipient" may be the same subject. Exemplary cells suitable for use in these embodiments include mobilized hematopoietic stem cells, PBMCs, dendritic cells, and the like. In some embodiments, the cells are chosen from those that naturally express self antigens that are targeted in the autoimmune disease. For example, type I diabetes is an autoimmune disease wherein the body reacts and rejects pancreatic islet (β) cells. In early stages of diabetes, before all islet cells are rejected, it can be possible to induce tolerance to islet cells and thereby prevent the progression of diabetes.

In specific embodiments, host-derived cells are decorated with SA-FasL and/or SA-IL-2 and used either alone or in combination with soluble SA-FasL and/or IL-2. For example, host-derived cells can be decorated with SA-FasL and used with soluble SA-FasL, and optionally further with IL-2. In other embodiments, a dendritic cell is pulsed with autoantigen and decorated with SA-FasL and/or SA-IL-2 and used with soluble SA-FasL and/or soluble IL-2, to induce tolerance to the autoantigen. For example, dendritic cells can be pulsed with autoantigen and decorated with SA-FasL and used with soluble SA-FasL, and optionally further with IL-2.

In other embodiments cells, such as bone marrow, PBMCs, DCs, etc., are decorated with autoantigen and also decorated with SA-FasL, and optionally further with SA-IL2, and administered with soluble SA-FasL, and optionally further with IL-2 to treat autoimmunity.

In specific embodiments, the autoantigen is associated with diabetes, rheumatic fever, multiple sclerosis or lupus.
Medicaments and Compositions Some aspects of the invention relates to the surprising discovery that soluble SA-FasL, optionally further with IL-2, can be used to achieve long-term, specific immunosuppression. Further particular aspects of the invention relates to the surprising discovery that soluble SA-FasL, optionally further with IL-2, can be used with FasL-decorated cells to achieve long term and specific immunosuppression.

In some embodiments, there are provided medicaments for use in inducing immune tolerance in a subject in need thereof, comprising (i) a chimeric FasL protein comprising a FasL moiety and a streptavidin or avidin moiety and (ii) an IL-2 protein. In any embodiments, the chimeric FasL protein and IL-2 protein may be provided in separate compositions or in the same composition.

Unless otherwise specified, in any embodiments, the chimeric FasL protein may be selected from soluble chimeric FasL proteins comprising a FasL moiety and a streptavidin or avidin moiety and chimeric FasL-decorated cells comprising a chimeric FasL protein comprising a FasL moiety and a streptavidin or avidin moiety bound to a cell surface via a biotin moiety on the cell surface. One embodiment of chimeric FasL protein has the amino acid sequence of SEQ ID NO: 3.

Unless otherwise specified, in any embodiments, the IL-2 protein may be selected from soluble IL-2 proteins, soluble chimeric IL-2 proteins comprising an IL-2 moiety and a streptavidin or avidin moiety; and chimeric IL-2-decorated cells comprising a chimeric IL-2 protein comprising an IL-2 moiety and a streptavidin or avidin moiety bound to a cell surface via a biotin moiety on the cell surface. One embodiment of chimeric IL-2 protein has the amino acid sequence of SEQ ID NO: 9.

In some embodiments, the medicament comprises soluble chimeric FasL protein and soluble IL-2 protein or soluble chimeric IL-2 protein. In other embodiments, the medicament comprises chimeric FasL-decorated cells and soluble IL-2 protein or soluble chimeric IL-2 protein. In another, the medicament comprises soluble chimeric FasL protein and chimeric IL-2-decorated cells. In another, the medicament comprises chimeric FasL-decorated cells and chimeric IL-2-decorated cells. In specific embodiments, a medicament for use in inducing immune tolerance may comprise soluble chimeric FasL protein comprising a FasL moiety and a streptavidin or avidin moiety.

The medicaments are effective for inducing immunomodulation in subjects in need of such immunomodulation, and can be used in such methods. For example, when the subject is in need of treatment for type 1 diabetes, the decorated cells, if present, may be splenocytes, PBMC, bone marrow cells, mesenchymal stem cells, hematopoietic stem cells, stem cells, induced pluripotent stem cells, dendritic cells, and dendritic cells pulsed with autoantigens, and others as discussed above. When the subject is in need of the treatment or prevention of allograft rejection, the decorated cells, if present, may be cells from the allograft donor, such as cells selected from the group consisting of allograft bone marrow cells, allograft cardiac myocytes and allograft vascular cells, or other cells from the allograft donor as discussed above.

One embodiment of the presently-disclosed subject matter is directed to a pharmaceutical composition or medicament comprising (a) cells comprising biotin on their surface, (b) a chimeric protein comprising (i) an apoptosis-inducing FasL moiety and (ii) a member of a binding pair selected from the group consisting of avidin and streptavidin moieties; wherein the chimeric protein of (b) is bound through the avidin or streptavidin moiety to biotin on the surface of said cells of (a), and (c) a chimeric protein comprising (i) an apoptosis-inducing FasL moiety and (ii) a member of a binding pair selected from the group consisting of avidin and streptavidin moieties, wherein the chimeric protein of (c) is in soluble form. In some embodiments, the chimeric proteins of (b) and (c) form tetramers and/or oligomers. In some embodiments, the composition comprises an amount of these components effective to induce immune tolerance when administered to a subject in need thereof.

Another embodiment of the presently-disclosed subject matter is directed to a pharmaceutical composition or medicament comprising (a) cells comprising biotin on their surface, (b) a chimeric protein comprising (i) an apoptosis-inducing FasL moiety and (ii) a member of a binding pair selected from the group consisting of avidin and streptavidin moieties; wherein the chimeric protein of (b) is bound through the avidin or streptavidin moiety to biotin on the surface of said cells of (a), and (c) soluble IL-2. In some embodiments, the composition comprises an amount of these components effective to induce immune tolerance when administered to a subject in need thereof.

An additional embodiment is directed to a pharmaceutical composition or medicament comprising (a) cells comprising biotin on its surface, (b) a chimeric protein comprising (i) an apoptosis-inducing FasL moiety and (ii) a member of a binding pair selected from the group consisting of avidin and streptavidin moieties; (c) a chimeric protein comprising (i) an IL-2 moiety and (ii) a member of a binding pair selected from the group consisting of avidin and streptavidin moieties wherein the chimeric proteins of (b) and (c) are bound through the avidin or streptavidin moiety to biotin on the surface of said cells of (a). In some embodiments, the composition comprises an amount of these components effective to induce immune tolerance when administered to a subject in need thereof.

In some embodiments, the FasL moiety is positioned C-terminal to the binding pair member moiety. In other embodiments, the FasL moiety is positioned N-terminal to the binding pair member moiety. In any embodiments, the member of a binding pair may be streptavidin or core streptavidin. In some embodiments, the chimeric FasL protein forms tetramers and/or oligomers.

The FasL moiety may be wild type FasL (wtFasL includes any mammalian FasL, including rat, mouse, or human wild type FasL), modified FasL (mFasL includes any mammalian FasL modified to be stably expressed on a cell surface), or soluble (sFasL soluble includes the extracellular portion of any mammalian FasL). In any embodiments, a construct comprising a FasL moiety can further include one or more linkers, zinc zippers, can be pegylated, etc.

In some embodiments, a construct comprising a FasL moiety is capable of binding through the FasL moiety to a cell expressing a death receptor. If the construct is bound via a member of a binding pair to a cell, the construct may be capable of binding to a further cell expressing a death receptor through the FasL moiety.

In any embodiments of a construct comprising IL-2, the construct may be a soluble IL-2 construct, such as a chimeric protein comprising (i) an IL-2 moiety and (ii) a member of a binding pair selected from the group consisting of avidin and streptavidin moieties. In any embodiments, the member of a binding pair may be streptavidin or core streptavidin. The IL-2 moiety may be positioned C-terminal or N-terminal to the binding pair member moiety. In some embodiments, the chimeric IL-2 protein forms tetramers and/or oligomers.

The IL-2 moiety may be wtIL-2 (including any mammalian IL-2, including rat, mouse, or human wild type IL-2 molecule), mIL-2 (including any mammalian IL-2 modified to be stably expressed on the cell surface), or sIL-2 (including the soluble extracellular portion of any mammalian IL-2). In any embodiments, the construct comprising an IL-2 moiety can further include one or more linkers, zinc zippers, can be pegylated, etc.

In some embodiments, a construct comprising an IL-2 moiety is capable of binding through the IL-2 moiety to a cell expressing an IL-2 receptor. If the construct is bound via a member of a binding pair to a cell, the construct may be capable of binding to a further cell expressing an IL-2 receptor through the FasL moiety.

In some embodiments, any pharmaceutical composition or medicament described herein may further comprise an alloantigen and/or an autoantigen. In some embodiments, the alloantigen is a cell. In particular embodiments, the cell is a mammalian cell. In certain embodiments, the alloantigen is a pancreatic islet cell, a tissue, or an organ. In other embodiments, the cell of the pharmaceutical composition is selected from the group consisting of islet cells, bone marrow cells, hematopoietic stem cells, stem cell, induced pluripotent stem cell, human beta cell products, hepatocytes, dendritic cells, PBMC, macrophages, endothelial cells, mesenchymal stem cell, and immune cells, including T cells. In even further embodiments, the cell is part of a tissue or organ. Other embodiments of cells are discussed above.

A further embodiment of the presently-disclosed subject matter is directed to medicaments comprising (a) a chimeric protein comprising (i) an apoptosis-inducing FasL moiety and (ii) a member of a binding pair selected from the group consisting of avidin and streptavidin moieties, wherein the chimeric protein of (a) is in soluble form, and (b) soluble IL-2. In some embodiments, the composition comprises an amount of these components effective to induce immune tolerance when administered to a subject in need thereof.

The chimeric proteins may be provided in separate compositions, or in a single composition. Each composition may further comprise a pharmaceutically acceptable carrier, excipient or diluent, as known in the art. Consistent with the conventions in the art, a pharmaceutically acceptable carrier may be a material that can be used as a vehicle for the active agents in the composition because the carrier material is inert or otherwise medically acceptable, as well as compatible with the active agent(s), in the context of formulation, storage, and administration. A pharmaceutically acceptable carrier can contain conventional pharmaceutical additives like diluents and preservatives.

Methods

The invention also includes methods for inducing immune tolerance. In some embodiments, the method of inducing immune tolerance in a subject in need thereof comprises administering to the individual (i) a chimeric FasL protein comprising a FasL moiety and a streptavidin or avidin moiety and (ii) an IL-2 protein. The FasL protein and the IL-2 protein may be administered together or separately, in any order. In any such embodiments, the FasL may be selected from soluble chimeric FasL proteins comprising a FasL moiety and a streptavidin or avidin moiety and chimeric FasL-decorated cells comprising a chimeric FasL protein comprising a FasL moiety and a streptavidin or avidin moiety bound to a cell surface via a biotin moiety on the cell surface, where the FasL moiety may be any FasL moiety discussed above.

The IL-2 protein may be selected from the group consisting of soluble IL-2 proteins, soluble chimeric IL-2 proteins comprising an IL-2 moiety and a streptavidin or avidin moiety; and chimeric IL-2-decorated cells comprising a chimeric IL-2 protein comprising an IL-2 moiety and a streptavidin or avidin moiety bound to a cell surface via a biotin moiety on the cell surface, where the IL-2 moiety may be any IL-2 moiety discussed above.

Such methods may be practiced on a subject in need of treatment for type 1 diabetes, wherein the decorated cells, if present, are PBMCs, splenocytes, bone marrow cells, mesenchymal stem cells, hematopoietic stem cells, stem cells, dendritic cells, or induced pluripotent stem cells, or other suitable cells such as discussed above. For example, such a method may comprise administering to the subject in need thereof:

(a) chimeric FasL-decorated pancreatic islet cells;
(b)(i) soluble chimeric FasL protein and (ii) soluble IL-2 protein or soluble chimeric IL-2 protein, in amounts effective to induce immune tolerance to pancreatic islet cells; and
(c) optionally, administering an immunosuppressant, such as rapamycin.

In further embodiments, the subject is in need of the treatment or prevention of allograft rejection and the decorated cells, if present, are cells from the allograft donor, such as cells selected from the group consisting of allograft bone marrow cells, allograft cardiac myocytes and allograft vascular cells, or other cells from the allograft donor, as discussed above. For example, such a method of treating or preventing allograft rejection in a subject in need thereof, may comprise:

(a) administering chimeric FasL-decorated cells from the allograft donor, such as cells selected from the group consisting of allograft bone marrow cells, allograft cardiac myocytes and allograft vascular cells, or other cells from the allograft donor;
(b) administering (i) soluble chimeric FasL protein and (ii) soluble IL-2 protein or soluble chimeric IL-2 protein, in amounts effective to induce immune tolerance to the allograft cells; and
optionally, administering an immunosuppressant, such as rapamycin.

In specific embodiments of any of these methods, the allograft may be decorated with one or both FasL and IL-2.

In specific embodiments of any of these methods, the chimeric FasL protein may have the amino acid sequence of SEQ ID NO: 3. Independently, in specific embodiments of any of these methods, the chimeric IL-2 may have the amino acid sequence of SEQ ID NO: 9.

Further embodiments are directed to methods of inducing immune modulation in a mammal in need thereof comprising administering an effective amount of any pharmaceutical composition or medicament as described herein to a mammal having a condition which is alleviated by the apoptosis of activated pathogenic lymphocytes. In certain embodiments of a method of inducing immune modulation in a mammal in need thereof, the mammal has a condition which is alleviated by the apoptosis of activated pathogenic lymphocytes and the induction/expansion of protective lymphocytes, such as T regulatory cells. In other embodiments, the mammal can have a genetically inherited hematopoietic metabolic disorder or cancer. In certain embodiments of a method of inducing immune modulation in a mammal in need thereof, the mammal has a condition selected from the group consisting of asthma, allergy, food poisoning, autoimmunity, and transplantation of allogeneic or xenogeneic cells, tissues, and organs. For example, bone marrow transplantation is a critical tool in the treatment of leukemia and other cancers. Stem cell transplants show promise to repair damaged or degenerated tissue, and therefore tolerance to donor stem cells is advantageous, Other situations where tolerance to donor tissues, organs or cells is advantageous include heart transplants, kidney transplants, liver transplants, vascular transplants, skin transplants, and blood transfusions. The methods described herein can be used in such contexts.

In more specific embodiments, the autoimmune condition is selected from the group consisting of diabetes, multiple sclerosis, lupus erythematosis, sarcoidsis, Sjögren's syndrome, polymyalgia rheumatica, ankylosing spondylitis, alopecia areata, and rheumatoid arthritis. autoimmune hematological disorders (including e.g. hemolytic anaemia, aplastic anaemia, pure red cell anaemia and idiopathic thrombocytopenia), systemic lupus erythematosus, polychondritis, sclerodoma, Wegener granulomatosis, dermatomyositis, chronic active hepatitis, myasthenia gravis, psoriasis, Steven-Johnson syndrome, idiopathic sprue, (autoimmune) inflammatory bowel disease (including e.g. ulcerative colitis and Crohn's disease), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis. Accumulating data indicate that many chronic diseases, such as Type 2 diabetes atherosclerosis, may be caused by immune dysregulation, i.e. pathogenic/regulatory cell imbalance. Autoimmune and inflammatory conditions of the skin are also considered to be amenable to treatment and prevention using the synergistic combination of the invention, e.g., psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, and other inflammatory or allergic conditions of the skin, as are inflammatory conditions of the lungs and airways including asthma, allergies, and pneumoconiosis.

When preventing or treating autoimmunity in a subject in need thereof, the method may comprise (a) administering to the subject cells decorated with chimeric FasL and optionally decorated with chimeric IL-2, and (b) administering (i) soluble chimeric FasL protein and (ii) soluble IL-2 protein or soluble chimeric IL-2 protein, in amounts effective to induce immune tolerance to the autoantigen; wherein the cells are selected from (i) a cell expressing an autoantigen (ii) a cell decorated with an autoantigen and (ii) a dendritic cell pulsed with the autoantigen. In particular embodiments, the cell expressing an autoantigen or the cell decorated with the autoantigen is obtained from the patient, and is selected from bone marrow cells, dendritic cells, PBMC, hematopoietic stem cells, or other cells as discussed above.

In accordance with further embodiments, there are provided methods of treating or preventing autoimmunity in a subject in need thereof, comprising (a) administering an autoantigen presented on a cell selected from the group consisting of (i) a cell expressing the autoantigen (ii) a cell decorated with the autoantigen and (iii) a dendritic cell pulsed with the autoantigen, wherein the cell optionally is decorated with chimeric FasL and/or chimeric IL-2, and (b) administering (i) soluble chimeric FasL protein and (ii) soluble IL-2 protein or soluble chimeric IL-2 protein, in amounts effective to induce immune tolerance to the autoantigen. In particular embodiments, the cell is obtained from the subject. In specific embodiments, the cell is selected from bone marrow cells, dendritic cells, PBMC, hematopoietic stem cells, and mesenchymal stem cells, including any of such cells obtained from the subject.

In specific embodiments of any of these methods, the chimeric FasL protein may have the amino acid sequence of SEQ ID NO: 3. Independently, in specific embodiments of any of these methods, the chimeric IL-2 may have the amino acid sequence of SEQ ID NO: 9.

In any embodiments, the method may further comprise administering an effective amount of an immunomodulatory drug. Exemplary immunomodulatory drugs include rapamycin and cyclophosamide. Other non-limiting examples include busulfan, fludarabine, methotrexate, sulfasalazine, hydroxychloroquine, azathioprine, tocilizumab, etanercept, adalimumab, anakinra, abatacept, rituximab, certolizumab, golimumab, cyclosporine, dexamethasone, methylprednisolone, predinisone, and triamcinolone.

Absolute dosages of the compounds will vary depending on the individual, the route of administration and the nature and severity of the condition to be treated. Generally speaking, the dosages of FasL and IL-2 reported in the examples, as used in mice, can be converted to human dosages according to the following table:

|  |  | TO |  |  |  |  |
|---|---|---|---|---|---|---|
|  |  | Mouse 20 g | Rat 150 g | Monkey 3 kg | Dog 8 kg | Man 60 kg |
| FROM | Mouse | 1 | ½ | ¼ | ⅙ | 1/12 |
|  | Rat | 2 | 1 | ½ | ¼ | 1/7 |
|  | Monkey | 4 | 2 | 1 | ⅗ | ⅓ |
|  | Dog | 6 | 4 | 1⅔ | 1 | ½ |
|  | Man | 12 | 7 | 3 | 2 | 1 |

Furthermore, the dosage necessary to induce apoptosis may depend on the affinity and specificity of the apoptotic agent. The amount of apoptotic agent administered also may vary with the number of cells being treated.

Generally speaking, the methods described herein using FasL may include administering FasL doses of from less than about 0.2 µg/day/patient to at least about 10 µg/day/patient, or more, based on the FasL moiety. For example, methods described herein may be carried out using daily doses of FasL at amounts of less than about 0.2 µg/day/patient, about 0.2 µg/day/patient, about 0.5 µg/day/patient, about 1 µg/day/patient, about 1.5 µg/day/patient, about 2 µg/day/patient, about 2.5 µg/day/patient, about 3 µg/day/patient, about 3.5 µg/day/patient, about 4 µg/day/patient, about 4.5 µg/day/patient, about 5 µg/day/patient, or more.

Generally speaking, the methods described herein using IL-2 may include administering IL-2 at daily doses ranging from less than about 5000 IU/day/patient to at least about 30000000 IU/day/patient, or more, based on the IL-2 moiety. For example, methods described herein may be carried out using daily IL-2 doses of less than about 5000 IU/day/patient, about 5000 IU/day/patient, about 10000 IU/day/patient, about 25000 IU/day/patient, about 50000 IU/day/patient, about 100000 IU/day/patient, 200000 IU/day/patient, 500000 IU/day/patient, 1000000 IU/day/patient, 2000000 IU/day/patient, 30000000 IU/day/patient, or more.

As noted above, these dosages are illustrative only. The dosage and schedule of administration may vary within and even from these ranges depending on the aim of the treatment, the disease to be treated, the specific subject, etc.

In some embodiments, the treatment is administered over a course of several days, for example over 1-30 days, including from about 7 to about 15 days, for about 1 week, or for about 2 weeks. As with dosage, the duration of treatment may vary within and even from these ranges depending on the aim of the treatment, the disease to be treated, the specific subject, etc.

Additional Specific Embodiments

Specific embodiments of the compositions and methods described herein include:

E1. A pharmaceutical composition comprising an effective amount of: (a) a cell comprising biotin on its surface, (b) a chimeric protein comprising (i) an apoptosis-inducing FasL moiety and (ii) a member of a binding pair selected from the group consisting of avidin and streptavidin moieties; wherein the chimeric protein of (b) is bound through the avidin or streptavidin moiety to biotin on the surface of said cells of (a), and (c) a chimeric protein comprising (i) an apoptosis-inducing FasL moiety and (ii) a member of a binding pair selected from the group consisting of avidin and streptavidin moieties, wherein the chimeric protein of (c) is in soluble form.

E2. The pharmaceutical composition of embodiment 1, wherein the apoptosis-inducing FasL moiety of (b) and (c) are wtFasL, mFasL, or sFasL.

E3. The pharmaceutical composition of embodiment 1, wherein the chimeric proteins of (b) and (c) bind through the FasL moiety to a further cell expressing a death receptor.

E4. The pharmaceutical composition of embodiment 1, wherein the chimeric proteins of (b) and (c) form tetramers and/or oligomers.

E5. The pharmaceutical composition of embodiment 1, wherein the member of a binding pair of (b) and (c) is streptavidin.

E6. The pharmaceutical composition of embodiment 5, wherein the streptavidin is core streptavidin.

E7. The pharmaceutical composition of embodiment 2, wherein the FasL of (b) and (c), is wtFasL, mFasL, or sFasL.

E8. The pharmaceutical composition of embodiment 1, wherein the apoptosis-inducing FasL moiety of (b) and (c) is positioned C-terminal or N-terminal to the binding pair member moiety.

E9. The pharmaceutical composition of embodiment 1, wherein said chimeric proteins of (b) and (c) consist essentially of (i) an apoptosis-inducing FasL moiety and (ii) a member of a binding pair selected from the group consisting of avidin and streptavidin moieties.

E10. The pharmaceutical composition of embodiment 1, wherein the cell of (a) is selected from a splenocyte, a PBMC, and a bone marrow cell.

E11. The pharmaceutical composition of embodiment 1, further comprising an alloantigen or autoantigen.

E12. The pharmaceutical composition of embodiment 11, wherein the alloantigen is a cell.

E13. The pharmaceutical composition of embodiment 11, wherein the alloantigen is a pancreatic islet cell, a tissue, or an organ.

E14. The pharmaceutical composition of embodiment 1, wherein the cell of (a) is selected from the group consisting of islet cells, bone marrow cells, hematopoietic stem cells, stem cell, induced pluripotent stem cell, human beta cell products, hepatocytes, dendritic cells, mesenchymal cells, macrophages, endothelial cells, and T cells.

E15. The pharmaceutical composition of embodiment 1, wherein the cell of (a) is part of a tissue or organ.

E16. A method of inducing immune modulation in a mammal in need thereof comprising administering an effective amount of the pharmaceutical composition of embodiment 1 to a mammal having a condition which is alleviated by the apoptosis of activated pathogenic lymphocytes.

E17. The method of embodiment 16, wherein the mammal has a condition selected from the group consisting of asthma, allergy, food poisoning, autoimmunity, and transplantation of allogeneic or xenogeneic tissue.

E18. The method of embodiment 17, wherein the autoimmune condition is selected from the group consisting of diabetes, multiple sclerosis, lupus erythematosis, sarcoidsis, and rheumatoid arthritis.

E19. The method of embodiment 16, further comprising administering an effective amount of rapamycin.

E20. The method of embodiment 19, further comprising administering an effective amount of cyclophosamide.

E21. A pharmaceutical composition comprising an effective amount of: (a) a cell comprising biotin on its surface, (b) a chimeric protein comprising (i) an apoptosis-inducing FasL moiety and (ii) a member of a binding pair selected from the group consisting of avidin and streptavidin moieties; wherein the chimeric protein of (b) is bound through the avidin or streptavidin moiety to biotin on the surface of said cells of (a), and (c) soluble IL-2.

E22. The pharmaceutical composition of embodiment 21, wherein the apoptosis-inducing FasL moiety of (b) is wtFasL, mFasL, or rsFasL.

E23. The pharmaceutical composition of embodiment 21, wherein the soluble IL-2 is a chimeric protein comprising (i) an IL-2 moiety and (ii) a member of a binding pair selected from the group consisting of avidin and streptavidin moieties.

E24. The pharmaceutical composition of embodiment 23, wherein the IL-2 moiety of (c) is wtIL-2 or sIL-2.

E25. The pharmaceutical composition of embodiment 21, wherein the chimeric protein of (b) binds through the FasL moiety to a further cell expressing a death receptor.

E26. The pharmaceutical composition of embodiment 23, wherein the chimeric IL-2 protein of (c) binds through the IL-2 moiety to a further cell expressing an IL-2 receptor.

E27. The pharmaceutical composition of embodiment 21, wherein the chimeric protein of (b) forms tetramers and/or oligomers.

E28. The pharmaceutical composition of embodiment 23, wherein the chimeric IL-2 protein forms tetramers and/or oligomers.

E29. The pharmaceutical composition of embodiment 21, wherein the member of a binding pair of (b) and is streptavidin.

E30. The pharmaceutical composition of embodiment 23, wherein the member of a binding pair of the chimeric IL-2 protein is streptavidin.

E31. The pharmaceutical composition of embodiment 29, wherein the streptavidin is core streptavidin.

E32. The pharmaceutical composition of embodiment 30, wherein the streptavidin is core streptavidin.

E33. The pharmaceutical composition of embodiment 22 wherein the FasL of (b), is mFasL.

E34. The pharmaceutical composition of embodiment 21, wherein the apoptosis-inducing FasL moiety of (b) is positioned C-terminal to the binding pair member moiety.

E35. The pharmaceutical composition of embodiment 23, wherein the IL-2 moiety is positioned N-terminal to the binding pair member moiety.

E36. The pharmaceutical composition of embodiment 21, wherein said chimeric protein of (b) consists essentially of (i) an apoptosis-inducing FasL moiety and (ii) a member of a binding pair selected from the group consisting of avidin and streptavidin moieties.

E37. The pharmaceutical composition of embodiment 23, wherein said chimeric IL-2 protein consists essentially of (i) an IL-2 moiety and (ii) a member of a binding pair selected from the group consisting of avidin and streptavidin moieties.

E38. The pharmaceutical composition of embodiment 21, wherein the cell of (a) is a splenocyte or peripheral blood mononuclear cell (PBMC).

E39. The pharmaceutical composition of embodiment 21, further comprising an alloantigen or autoantigen.

E40. The pharmaceutical composition of embodiment 39, wherein the alloantigen is a cell.

E41. The pharmaceutical composition of embodiment 39, wherein the alloantigen is a pancreatic islet cell, a tissue, or an organ.

E42. The pharmaceutical composition of embodiment 21, wherein the cell of (a) is selected from the group consisting of islet cells, bone marrow cells, hematopoietic stem cells, human beta cell products, hepatocytes, dendritic cells, mesenchymal cells, macrophages, endothelial cells, and T-cells.

E43. The pharmaceutical composition of embodiment 21, wherein the cell of (a) is part of a tissue or organ.

E44. A method of inducing immune modulation in a mammal in need thereof comprising administering an effective amount of the pharmaceutical composition of embodiment 21 to a mammal having a condition which is alleviated by the apoptosis of activated pathogenic lymphocytes.

E45. The method of embodiment 44, wherein the mammal has a condition selected from the group consisting of asthma, allergy, food poisoning, autoimmunity, and transplantation of allogeneic or xenogeneic tissue.

E46. The method of embodiment 45, wherein the autoimmune condition is selected from the group consisting of diabetes, multiple sclerosis, lupus erythematosis, sarcoidsis, and rheumatoid arthritis.

E47. The method of embodiment 44, further comprising administering an effective amount of a chimeric protein comprising (i) an apoptosis-inducing FasL moiety and (ii) a member of a binding pair selected from the group consisting of avidin and streptavidin moieties, wherein the chimeric protein is in soluble form.

E48. The method of embodiment 47, further comprising administering an effective amount of rapamycin.

E49. The method of embodiment 48, further comprising administering an effective amount of cyclophosphamide.

E50. A pharmaceutical composition comprising an effective amount of: (a) a chimeric protein comprising (i) an apoptosis-inducing FasL moiety and (ii) a member of a binding pair selected from the group consisting of avidin and streptavidin moieties, wherein the chimeric protein of (a) is in soluble form, and (b) soluble IL-2.

E51. The pharmaceutical composition of embodiment 50, wherein the apoptosis-inducing FasL moiety of (a) is wtFasL, mFasL, or sFasL.

E52. The pharmaceutical composition of embodiment 50, wherein the soluble IL-2 is a chimeric protein comprising (i) an IL-2 moiety and (ii) a member of a binding pair selected from the group consisting of avidin and streptavidin moieties.

E53. The pharmaceutical composition of embodiment 52, wherein the IL-2 moiety of (b) is wtIL-2, m-IL-2, or sIL-2.

E54. The pharmaceutical composition of embodiment 50 wherein the chimeric protein of (a) binds through the FasL moiety to a further cell expressing a death receptor.

E55. The pharmaceutical composition of embodiment 52, wherein the chimeric IL-2 protein of binds through the IL-2 moiety to a further cell expressing an IL-2 receptor.

E56. The pharmaceutical composition of embodiment 50, wherein the chimeric protein of (a) forms tetramers and/or oligomers.

E57. The pharmaceutical composition of embodiment 52, wherein the chimeric IL-2 protein forms tetramers and/or oligomers.

E58. The pharmaceutical composition of embodiment 50, wherein the member of a binding pair of (a) is streptavidin.

E59. The pharmaceutical composition of embodiment 52, wherein the member of a binding pair of the chimeric IL-2 protein is streptavidin.

E60. The pharmaceutical composition of embodiment 58, wherein the streptavidin is core streptavidin.

E61. The pharmaceutical composition of embodiment 59, wherein the streptavidin is core streptavidin.

E62. The pharmaceutical composition of embodiment 51 wherein the FasL of (a) is sFasL.

E63. The pharmaceutical composition of embodiment 50, wherein the apoptosis-inducing FasL moiety of (a) is positioned C-terminal to the binding pair member moiety.

E64. The pharmaceutical composition of embodiment 52, wherein the IL-2 moiety is positioned N-terminal to the binding pair member moiety.

E65. The pharmaceutical composition of embodiment 50, wherein said chimeric protein of (a) consists essentially of (i) an apoptosis-inducing FasL moiety and (ii) a member of a binding pair selected from the group consisting of avidin and streptavidin moieties.

E66. The pharmaceutical composition of embodiment 52, wherein said chimeric IL-2 protein consists essentially of (i) an IL-2 moiety and (ii) a member of a binding pair selected from the group consisting of avidin and streptavidin moieties.

E67. The pharmaceutical composition of embodiment 50, further comprising an alloantigen or autoantigen.

E68. The pharmaceutical composition of embodiment 67, wherein the alloantigen is a cell.

E69. The pharmaceutical composition of embodiment 67, wherein the alloantigen is a pancreatic islet cell, a tissue, or an organ.

E70. A method of inducing immune modulation in a mammal in need thereof comprising administering an effective amount of the pharmaceutical composition of embodiment 50 to a mammal having a condition which is alleviated by the apoptosis of activated pathogenic lymphocytes.

E71. The method of embodiment 70, wherein the mammal has a condition selected from the group consisting of asthma, allergy, food poisoning, autoimmunity, and transplantation of allogeneic or xenogeneic tissue.

E72. The method of embodiment 71, wherein the autoimmune condition is selected from the group consisting of diabetes, multiple sclerosis, lupus erythematosis, sarcoidsis, and rheumatoid arthritis.

E73. The method of embodiment 70, further comprising administering an effective amount (a) a cell comprising biotin on its surface, (b) a chimeric protein comprising (i) a IL-2 moiety and (ii) a member of a binding pair selected from the group consisting of avidin and streptavidin moieties; wherein the chimeric protein of (b) is bound through the avidin or streptavidin moiety to biotin on the surface of said cells of (a).

E74. The method of embodiment 73, further comprising administering an effective amount of rapamycin.

E75. The method of embodiment 74, further comprising administering an effective amount of cyclophosphamide.

E76. A pharmaceutical composition comprising an effective amount of: (a) a cell comprising biotin on its surface, (b) a chimeric protein comprising (i) an apoptosis-inducing FasL moiety and (ii) a member of a binding pair selected from the group consisting of avidin and streptavidin moieties; (c) a chimeric protein comprising (i) an IL-2 moiety and (ii) a member of a binding pair selected from the group consisting of avidin and streptavidin moieties wherein the chimeric proteins of (b) and (c) are bound through the avidin or streptavidin moiety to biotin on the surface of said cells of (a).

E77. The pharmaceutical composition of embodiment 76, wherein the apoptosis-inducing FasL moiety of (b) is wtFasL, mFasL, or sFasL.

E78. The pharmaceutical composition of embodiment 76, wherein the IL-2 moiety of (c) is wtIL-2, mIL-2, or sIL-2.

E79. The pharmaceutical composition of embodiment 76, wherein the chimeric protein of (b) binds through the FasL moiety to a further cell expressing a death receptor.

E80. The pharmaceutical composition of embodiment 76, wherein the chimeric IL-2 protein of (c) binds through the IL-2 moiety to a further cell expressing an IL-2 receptor.

E81. The pharmaceutical composition of embodiment 76, wherein the chimeric proteins of (b) and (c) forms tetramers and/or oligomers.

E82. The pharmaceutical composition of embodiment 76, wherein the member of a binding pair of (b) and (c) is streptavidin.

E83. The pharmaceutical composition of embodiment 82, wherein the streptavidin is core streptavidin.

E84. The pharmaceutical composition of embodiment 77 wherein the FasL of (b), is mFasL.

E85. The pharmaceutical composition of embodiment 78 wherein the IL-2 of (s), is mIL-2.

E86. The pharmaceutical composition of embodiment 76, wherein the apoptosis-inducing FasL moiety of (b) is positioned C-terminal to the binding pair member moiety.

E87. The pharmaceutical composition of embodiment 76, wherein the IL-2 moiety is positioned N-terminal to the binding pair member moiety.

E88. The pharmaceutical composition of embodiment 76, wherein said chimeric protein of (b) consists essentially of (i) an apoptosis-inducing FasL moiety and (ii) a member of a binding pair selected from the group consisting of avidin and streptavidin moieties.

E89. The pharmaceutical composition of embodiment 76, wherein said chimeric IL-2 protein consists essentially of (i) an IL-2 moiety and (ii) a member of a binding pair selected from the group consisting of avidin and streptavidin moieties.

E90. The pharmaceutical composition of embodiment 76, wherein the cell of (a) is a splenocyte.

E91. The pharmaceutical composition of embodiment 76, further comprising an alloantigen or autoantigen.

E92. The pharmaceutical composition of embodiment 91, wherein the alloantigen is a cell.

E93. The pharmaceutical composition of embodiment 91, wherein the alloantigen is a pancreatic islet cell, a tissue, or an organ.

E94. The pharmaceutical composition of embodiment 76, wherein the cell of (a) is selected from the group consisting of islet cells, bone marrow cells, hematopoietic stem cells, human beta cell products, hepatocytes, dendritic cells, mesenchymal cells, macrophages, endothelial cells, and T-cells.

E95. The pharmaceutical composition of embodiment 76, wherein the cell of (a) is part of a tissue or organ.

E96. A method of inducing immune modulation in a mammal in need thereof comprising administering an effective amount of the pharmaceutical composition of embodiment 76 to a mammal having a condition which is alleviated by the apoptosis of activated pathogenic lymphocytes.

E97. The method of embodiment 96, wherein the mammal has a condition selected from the group consisting of asthma, allergy, food poisoning, autoimmunity, and transplantation of allogeneic or xenogeneic tissue.

E98. The method of embodiment 97, wherein the autoimmune condition is selected from the group consisting of diabetes, multiple sclerosis, lupus erythematosis, sarcoidsis, and rheumatoid arthritis.

E99. The method of embodiment 96, further comprising administering an effective amount of a (a) chimeric protein comprising (i) an apoptosis-inducing FasL moiety and (ii) a member of a binding pair selected from the group consisting of avidin and streptavidin moieties, wherein the chimeric protein of is in soluble form and (b) soluble IL-2.

E100. The method of embodiment 99, further comprising administering an effective amount of rapamycin.

E101. The method of embodiment 100, further comprising administering an effective amount of cyclophosphamide.

E102. The method of embodiment 99, wherein the soluble IL-2 is a chimeric protein comprising (i) an IL-2 moiety and (ii) a member of a binding pair selected from the group consisting of avidin and streptavidin moieties.

EXAMPLES

The following examples are given by way of illustration and are in no way intended to limit the scope of the present invention.

Example 1 Construction, Expression, Characterization, and Cell Surface Decoration of SA-FasL and SA-IL-2

Construction of SA-FasL and SA-IL-2 and Expression in *Drosophila* S2 Cells.

Genomic DNA was isolated from *Streptomyces avidinii* (ATCC Cat.#27419) and 0.2 µg of this DNA was used as template for amplification using primers specific for the 5'-end and 3'-end of core streptavidin in PCR. The 5'-primer included sequences for BglII and 6 His residues (SEQ ID NO: 11) to allow cloning in frame with the *Drosophila* secretion signal (BiP) for expression as a secreted protein and purification using Ni-affinity columns. (Alternatively, Flag tag can be used instead of the 6 His residues (SEQ ID NO: 11), and anti-Flag Abs can be used for purification.) The PCR product was cloned into the TA cloning vector (Invitrogen, San Diego, CA) and several positive clones were identified by sequencing. We next subcloned the extracellular domain of rat FasL without the metalloproteinase site using a wild type FasL cDNA clone as a template and a sense primer to the 5'-end of the extracellular region, FasL6 (nucleotides 428-453) containing an EcoRI site, and an antisense primer to the 3'-end untranslated region of FasL, FasL2 (nucleotides 977-998) containing an EcoRI site in frame with SA, in PCR. Both the core streptavidin and extracellular FasL clones were digested out of the TA cloning vector with BglII-EcoRI for SA and EcoRI for extracellular FasL. These DNA inserts were then subcloned into the BglII-EcoRI-cut pMT/BiP/V5-His vector for expression in the DES™ system (Invitrogen).

*Drosophila* S2 cells were transfected with 20 µg of pMT/BiP/V5-His expression vector containing the SA-FasL recombinant gene in frame with the BiP secretion signal using the Calcium Phosphate Transfection kit according to the manufacturer's instructions (Invitrogen). Stable transfectants were established by cotransfection with 1 µg of pCoHYGRO vector and maintained in the presence of 300 µg/ml of hygromycin. SA-FasL expression was induced with 600 µM copper sulfate. Supernatant was collected 1-4 days after induction and either used immediately or precipitated with 50% ammonium persulfate, dialyzed against PBS, and purified using Ni-NTA columns (QIAGEN, Valencia, CA). The concentration of purified or culture supernatant SA-FasL was determined by the Bradford method or ELISA, respectively, using known amounts of commercially available streptavidin as standard. Similar methods can be used for the construction, expression, and purification of SA-IL-2.

Characterization of SA-FasL by Western Blot and ELISA.

The expression of SA-FasL by S2 cells was first detected using biotin-coated microwell strip plates in ELISA (Pierce, Rockford, IL). Briefly, biotinylated wells were incubated with culture supernatants collected after 96 hrs of induction of S2 cells with $CuSO_4$ for 45 min at room temperature. Wells were washed extensively, incubated with the working concentrations of primary antibodies against streptavidin or FasL (MFL4) for 45 min. Alkaline phosphatase- or HRP-conjugated secondary antibodies were used with the appropriate substrates to assess the amount of chimeric protein using an ELISA reader (Victor, Wallac, Gaithersburg, MD).

For Western blot analysis, culture supernatants were fractionated by PAGE under native and denaturing conditions and transferred onto PVDF membranes using a dry-blot apparatus (BioRad). Membranes were incubated with blocking buffer (5% dry milk and 0.5% Tween 20 in PBS), followed by incubation with rabbit anti-rat FasL serum (C-178; Santa Cruz, CA) at 1:1000 dilution in the blocking buffer for 1 hr. Membranes were then washed 3 times with washing buffer (0.2% Tween 20 in PBS) and incubated 1 hr with HRP-conjugated goat anti-rabbit antibody at 1:5000 dilution in blocking buffer (Pierce, Rockford, IL). Finally, membranes were washed several times and incubated in a chemiluminescent substrate according to the manufacturer's instructions (Molecular Dynamics, San Diego, CA).

Modification of the Cell Membrane with Biotin and Decoration with SA-FasL.

Various cell types were incubated in 1.5-150 µM freshly prepared EZ-Link™ Sulfo-NHS-LC-Biotin (Pierce) in PBS for 30 min at room temperature. Cells were washed twice and resuspended in PBS supplemented with 50-100 ng of SA-FasL per $10^6$ cells. After incubation on ice for 20-30 min with intermittent mixing, cells were washed twice and analyzed in flow cytometry using streptavidin-APC and MFL4 labeled with different fluorochromes to assess the cell-surface levels of biotin and SA-FasL, respectively. Similar methods were used to modify the cell membrane of cells with SA-IL-2.

Example 2 SA-FasL as a Soluble Protein for Immunomodulation

Immunomodulation with SA-FasL-engineered islets requires a short course of rapamycin treatment for tolerogenic efficacy (FIG. 1). This may be due to the limited amount of SA-FasL protein displayed on islets or short duration because of high turnover kinetics, thereby minimizing its tolerogenic effect. We, therefore, asked if SA-FasL can be used as a soluble protein to obviate the need for rapamycin. The use of SA-FasL as a soluble protein over the form attached to biological membranes for immunomodulation has various advantageous. First, the clinical and regulatory paths for using immunomodulatory biologics are well established. Second, the use of soluble biologics for therapy is practical as it involves simple injections. Third, the dose and treatment frequency and duration of soluble biologics can easily be established for the desired therapeutic outcome. Importantly, SA-FasL in soluble form may have wider applications as compared with the form fixed on biological surfaces.

Intraperitoneal treatment of graft recipients with 2-5 µg SA-FasL protein/mouse on days 1, 3, 5, 7 post-transplantation resulted in robust tolerogenic efficacy to allogeneic SA-FasL-islet grafts as only ⅛ had delayed rejection (~70 days; FIG. 1). Treatment with soluble SA-FasL only under a short course of rapamycin was also effective, achieving >80% graft survival.

Figure 2:
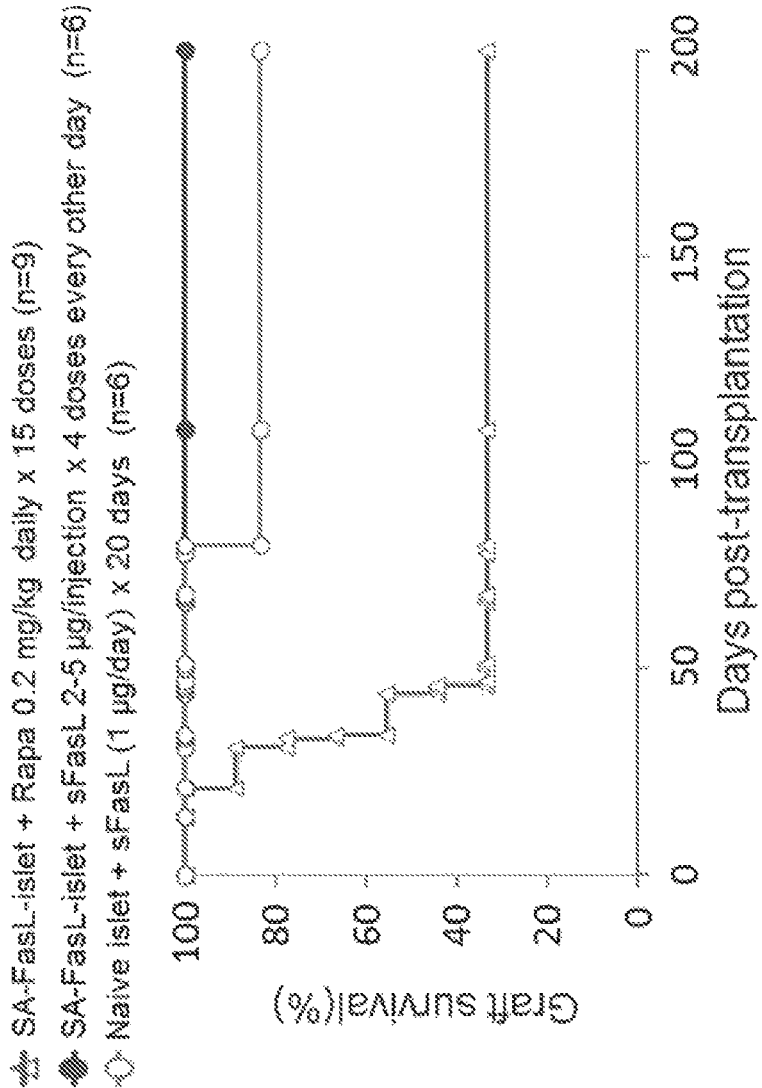
FIG. 2. Survival of allogeneic islets transplanted intraportally with different treatment protocols. BALB/c islets were engineered with SA-FasL protein and transplanted intraportally into STZ diabetic C57BL/6 mice. Rapa was used daily at 0.2 mg/kg for 15 doses starting on day of transplantation. Soluble (s)FasL was used at the indicated dose and regimens.

To further establish SA-FasL as a soluble biologic, we tested its immunomodulatory capacity for the prevention of allogeneic islets transplanted using a more stringent model of intraportal islet transplantation. The rationale for this model is twofold. First, intraportal islet transplantation is the only site practiced in the clinic. Second, intraportal islet transplantation provides a much more stringent model as compared to subrenal islet transplantation. As shown in FIG. 2, only 30% of recipients receiving allogeneic islets engineered with SA-FasL have long-term survival when transplanted intraportally in the BALB/c-to-C57BL/6 model. This is to be contrasted to 100% survival when SA-FasL-engineered islets transplanted under the kidney capsule. Therefore, we used this model to test if SA-FasL can be developed as a soluble biologic for the prevention and treatment of type I diabetes and foreign graft rejection. All BALB/c islets engineered with SA-FasL protein survived when 4 doses of SA-FasL (2-5 µg/injection) were administered into C57BL/6 recipients intravenously or intraperitoneally on days 1, 3, 5, and 7 post-transplantation. Indeed, the need for islet engineering with SA-FasL can also be overcome by systemic and protracted use of soluble FasL (1 µg injection daily for 20 days starting on day of transplantation). Only one out of six mice rejected the graft on day 80 post-transplantation.

These observations are important from two perspectives; i) for demonstrating that SA-FasL as monotherapy is sufficient to induce tolerance, but that the window of immunomodulation needs to be extended, and ii) SA-FasL can be used as a soluble biologic for immunomodulation at therapeutic doses without toxicity.

Figure 3:
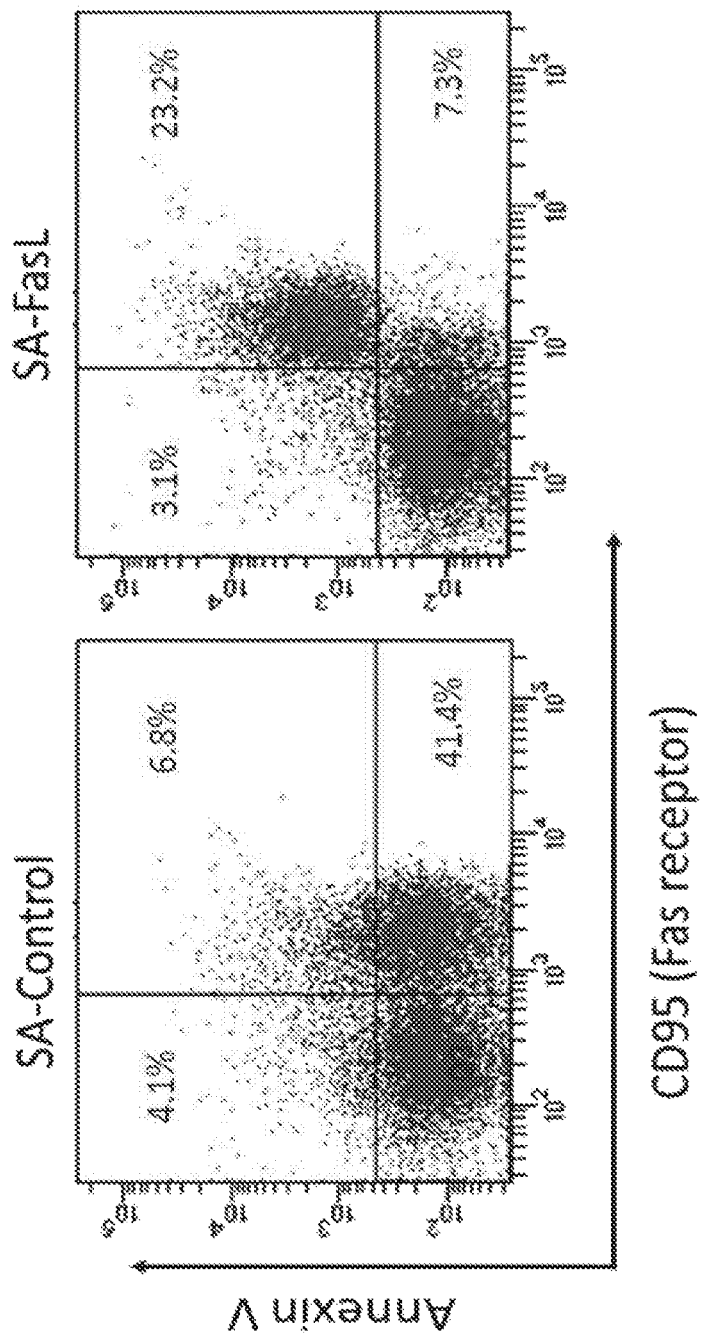
FIG. 3. SA-FasL induces apoptosis in nonhuman primate (NHP) Teff cells. NHP (rhesus monkey) PBMCs were cultured with SA-FasL and apoptosis was assessed using Annexin V by gating on $CD3^+$ T cells. Cells incubated with SA served as controls. Data is representative of PBMCs from 3 NHPs.

Example 3 SA-FasL as an Effective Immunomodulator to Control T Memory Responses Inasmuch as individuals with onset of autoimmunity have a large pool of activated and memory T cells, we asked if SA-FasL is capable of inducing apoptosis in such cells. For this purpose, we used nonhuman primate (NHP) peripheral blood lymphocytes (PBMCs). The PBMCs from 3 different NHPs were incubated with SA-FasL protein and apoptosis was assessed using flow cytometry. Almost all T cells expressing Fas underwent apoptosis irrespective of their phenotype, Teff ($CD3^+CD28^-Fas^+$) or T central ($CD3^+CD28^+Fas^+$) memory (FIG. 3).

Figure 4:
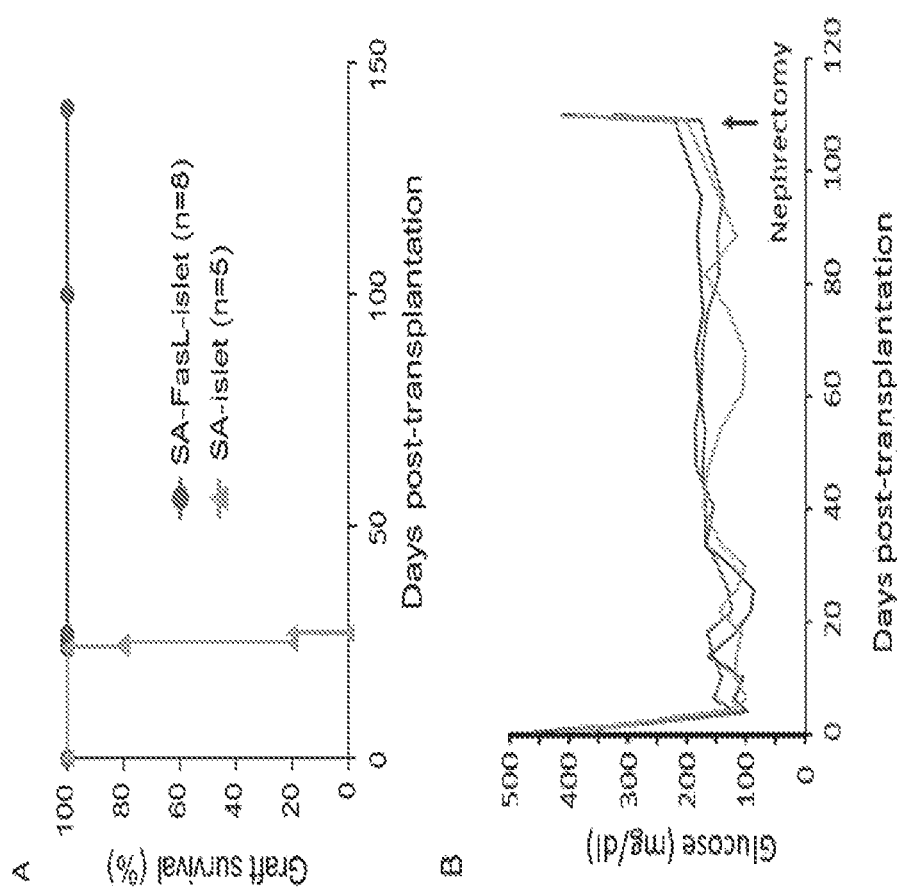
FIG. 4 A-B. SA-FasL-engineered islet grafts overcome rejection in recipients with established donor-specific immune memory. C57BL/6 mice were transplanted with BALB/c skin grafts on day 0, followed by STZ treatment and transplantation of BALB/c SA-FasL engineered islet grafts under the kidney capsule on day 40-50 post-skin transplantation. Mice transplanted with SA protein engineered islets (SA-islet) served as control. Rapamycin was given i.p. daily at 0.2 mg/kg for 15 doses starting on the day of islet transplantation. Graft survival is shown in FIG. 4A. The kidney bearing the transplanted islet graft was surgically removed for 3 mice in the SA-FasL group on day 109 post islet transplantation to confirm graft-dependent euglycemia (FIG. 4B). Animals were sacrificed 3 days post-nephrectomy after the confirmation of hyperglycemia.

To further provide in vivo data for efficacy of SA-FasL to overcome rejection in recipients with a large T cell memory pool, a set of C57BL/6 mice were transplanted with BALB/c skin grafts. These mice rejected skin grafts within 20 days. Mice were then made diabetic using STZ and transplanted with BALB/c SA-FasL-islet grafts 40-50 days post skin transplantation under transient cover of rapamycin. All mice remained euglycemic for an observation period over 140 days (FIG. 4A). Surgical removal of the kidney harboring islets resulted in prompt hyperglycemia, demonstrating that euglycemia was due to islet grafts (FIG. 4B). Taken together, these observations are important as various tolerance protocols fail to eliminate/control T memory cells, which serve as a major barrier for achieving clinical tolerance.

Example 4 SA-FasL as an Immunomodulator to Prevent Type 1 Diabetes

Figure 5:
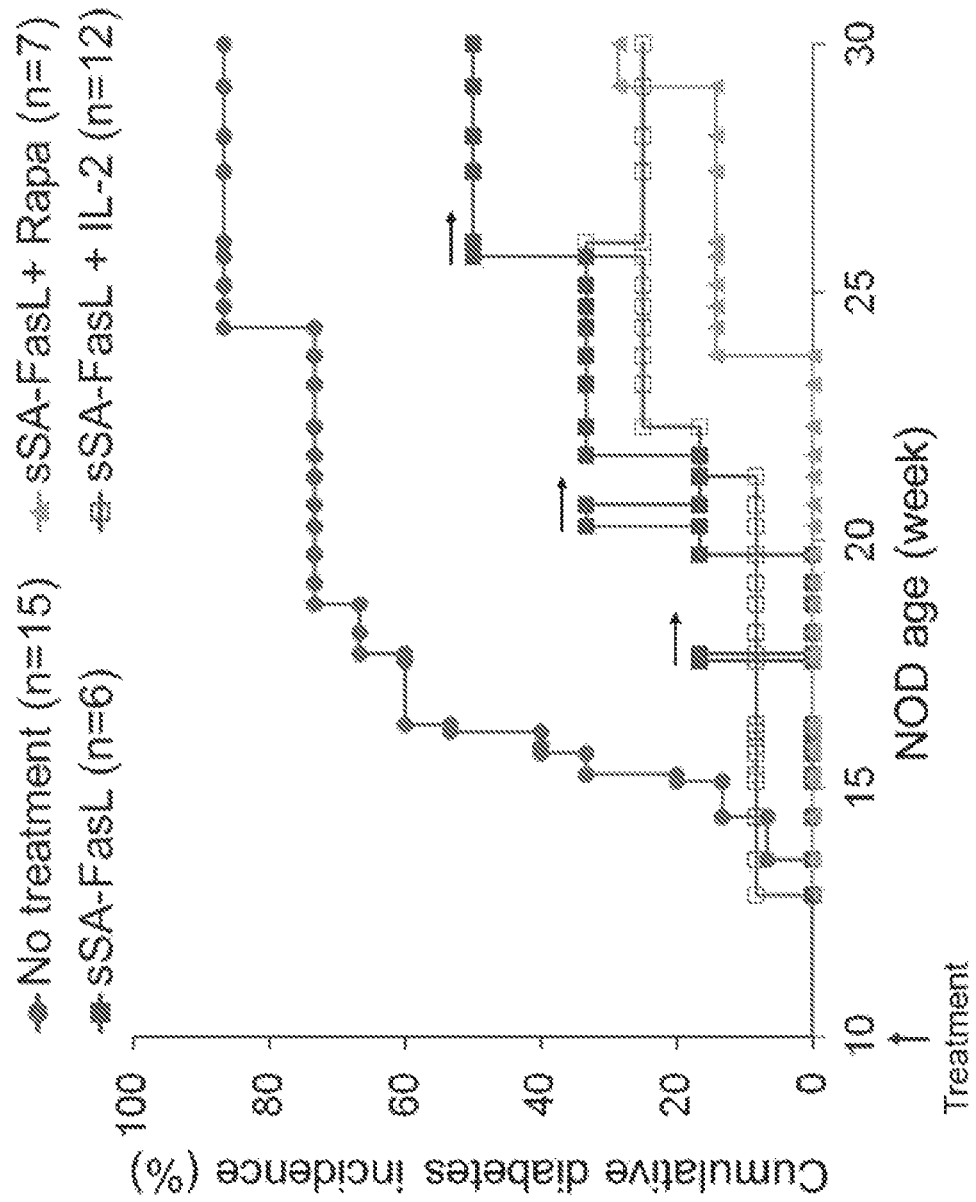
FIG. 5. Systemic treatment with SA-FasL protein delays the onset and incidence of Type 1 Diabetes in NOD. Female NOD mice were treated with the indicated agents at 10-week of age. Mice were then monitored for hyperglycemia by urine glucose test, which was confirmed by a blood glucose test. Mice with >200 mg/dl blood glucose levels were considered diabetic. Soluble (s)SA-FasL in PBS was used at 500 ng/injection intraperitoneally daily for 30 days. IL-2 was used at 3000 IU/injection daily for 30 days, whereas rapamycin was used daily at 0.2 mg/kg for 30 days. Female mice without any treatment were used as controls. In the SA-FasL only treatment group, 3 diabetic mice were treated with an additional 10 daily doses (black arrows) of SA-FasL soon after incidence of diabetes, resulting in temporary remission of hyperglycemia in ⅔ of those mice.

Inasmuch as antigen-experienced cells express Fas receptor on their surface, systemic treatment with SA-FasL has potential to eliminate such cells and control/reverse T1D without a major effect on quiescent T cell repertoire. This notion was tested by treating 10-wk female NOD mice daily with 500 ng SA-FasL protein for 30 days. As shown in FIG. 5, this treatment significantly delayed the onset and incidence of T1D as compared with controls. We did not observe any sign of SA-FasL toxicity. We next asked the question if SA-FasL will work in synergy with IL-2. Without being bound by theory, we hypothesized that IL-2 can further enhance FasL mediated apoptosis of T cells by various means, including down-regulating anti-apoptotic genes, such as cFLIP. In marked contrast, IL-2 is also critical growth and survival factor for T regulatory cells and T regulatory cells are resistant to Fas-mediated apoptosis due to the expression of high levels of anti-apoptotic genes, such as cFLIP. Indeed, T regulatory cells express FasL on their surface and control T effector responses by direct elimination via Fas receptor or indirectly by eliminating Fas-expressing DCs. Therefore, we hypothesized that the combinatorial use of SA-FasL and IL-2 may be effective in immune modulating auto and alloreactive responses for therapeutic purposes.

Treatment of female NOD (10-wk old) with a combination of SA-FasL and 3000 IU IL-2 daily for 30 days resulted in much improved delay of onset and incidence of diabetes. Indeed, the SA-FasL+IL-2 regimen performed as well as SA-FasL+rapamycin with respect to prevention of diabetes. These data demonstrate that SA-FasL is effective in delaying the onset and preventing the incidence of type 1 diabetes in NOD and works in synergy with IL-2 or rapamycin for a better outcome.

Figure 6A:
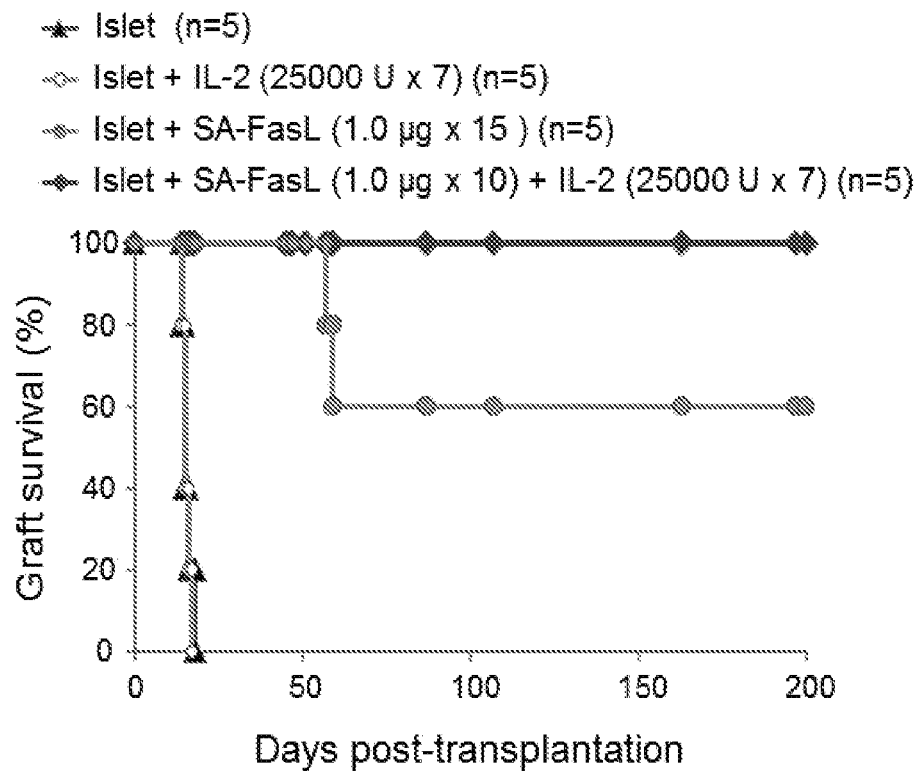
FIG. 6A-B. Combined use of SA-FasL and IL-2 prevents allogeneic islet graft rejection. BALB/c islets were transplanted intraportally into STZ diabetic age-matched males and females C57BL/6 mice. Recipients were treated with the indicated regimens of SA-FasL and IL-2 and monitored for graft rejection. In selected groups islets were either engineered with SA-FasL (SA-FasL-islet) or both SA-FasL and SA-IL2 (SA-FasL/SA-IL2-islet. Mice injected with soluble SA served as controls. Control islet and islet+IL-2 groups are the same for both panels for comparison purposes.
Figure 6B:
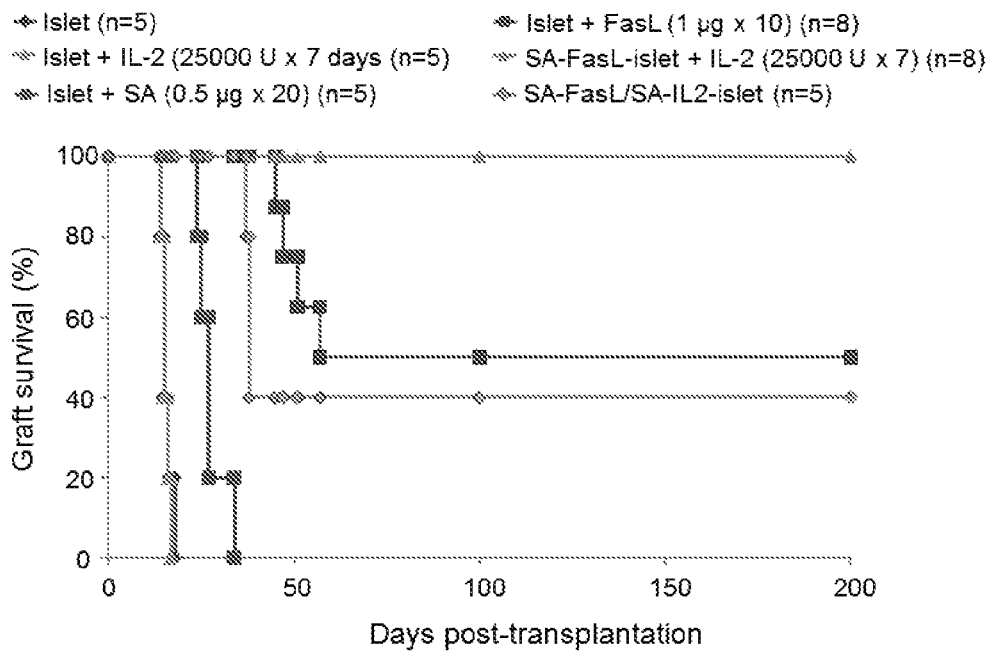

Example 5 SA-FasL Synergized with IL-2 to Promote Long-Term Survival of Transplanted Pancreatic Islets The combined use of soluble forms of SA-FasL and IL-2 in modulating immune response to autoantigens and preventing diabetes in NOD led us to test the combined use of these molecules as soluble biologics and a combination of soluble biologics and displayed on the surface of pancreatic islets. C57BL/6 mice were treated with intravenous injection of streptozotocin (200 mg/kg) and diabetes was confirmed by two consecutive blood glucose readings higher than 300 mg/dl. Pancreatic islets were harvested from BALB/c mice, cultured overnight, and then either left unmodified or engineered with SA-FasL alone or in combination with SA-IL2. These islets were then immediately transplanted intraportally into diabetic mice (450-550 islets/mouse). Mice were then treated with the indicated proteins and doses. Animals were monitored for diabetes, and those with two consecutive daily measurements of ≥250 mg/dl blood glucose level were considered diabetic and confirmation of graft failure. The data demonstrate that soluble SA-FasL as monotherapy prevents the rejection of ~60% of allogeneic islets and soluble IL-2 work in synergy and prevents the rejection in 100% of recipients long-term (FIG. 6A). Soluble IL-2 also works in synergy with SA-FasL on the surface of islet to prevent graft rejection in all graft recipients. Importantly, co-display of both SA-FasL and SA-IL2 was also effective in preventing rejection of ~40% of grafts (FIG. 6B).

Figure 7:
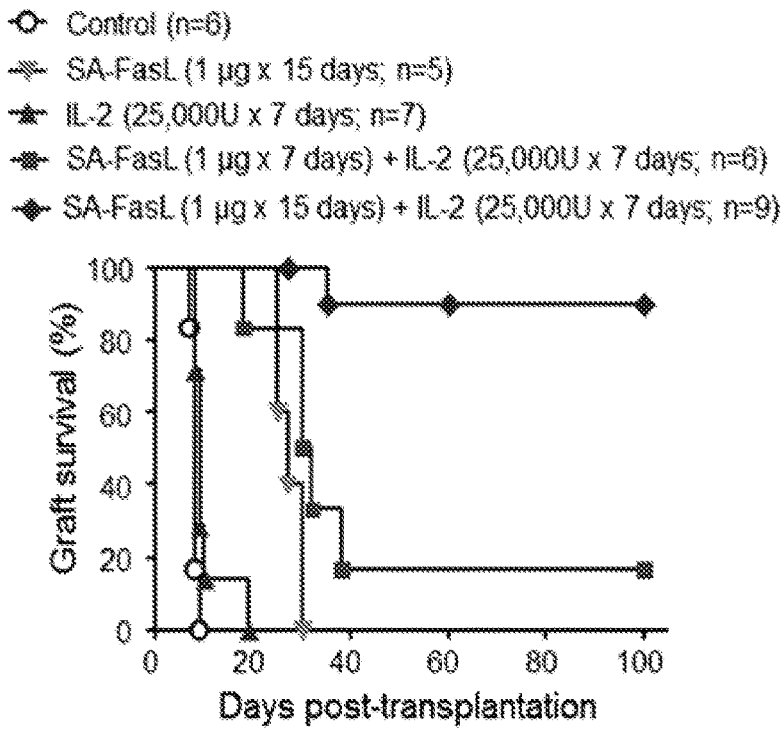
FIG. 7. Synergy between SA-FasL and IL-2 in inducing tolerance to cardiac allografts in the BALB/c-to-C57BL/6 model. C57BL/6 recipients of allogeneic BALB/c hearts were treated i.p. with the indicated doses of IL-2 and SA-FasL and mice were monitored for graft survival.

Example 6 SA-FasL Protein as a Biologic for the Prevention of Cardiac Allograft Rejection We next tested if SA-FasL as a biologic can work as an immunomodulator to prevent rejection of vascularized solid grafts. Heart transplantation from BALB/c into C57BL/6 mice was used as a stringent allogeneic heart graft model. C57BL/6 recipients of allogeneic BALB/c hearts were treated with a short course of IL-2 (7 doses) and SA-FasL (15 doses) without any other manipulation. As shown in FIG. 7, SA-FasL as monotherapy caused moderate prolongation of the grafts, while IL-2 did not have a significant effect. However, the combination of both molecules had robust tolerance effects with only 1 out of 9 grafts showing delayed rejection, whereas the rest survived for a 100-day observation period (data is from >3 independent experiments and hearts were scored in blind fashion by 2 individuals). We also demonstrated that soluble use of SA-FasL in combination with rapamycin was also effective in preventing cardiac graft rejection (Table 1).

The data shows that SA-FasL and IL-2 is surprisingly effective at inducing long term tolerance. The use of IL-2 by itself has no effect on inducing tolerance, but IL-2 synergistically enhances the effect of FasL in inducing long term tolerance to selected antigens. Therefore, the combined use of SA-FasL and IL-2 constitutes a major improvement in treating autoimmune disease and in inducing transplantation tolerance.

Example 7 SA-FasL Protein Work in Synergy with IL-2 to Prevent Bone Marrow Graft Rejection and Establish Mixed Hematopoietic Chimerism Bone marrow transplantation (BMT) as a source of hematopoietic stem cells is perceived as a powerful therapeutic regimen that can potentially treat a variety of inherited and acquired diseases, such as enzyme deficiencies, metabolic disorders, cancer. BMT leading to mixed allogeneic hematopoietic chimerism (MAHC) can be used as an immunomodulatory approach to induce tolerance to auto-, allo-, and xenoantigens for the treatment of autoimmune disorders and prevention of foreign graft rejection. Mixed chimeras are tolerant to both donor and host antigens since i) stem cells in the donor bone marrow give rise to immune cells, such as lymphocytes, that are "educated" in the host immune environment for nonresponsiveness to the host antigens and ii) macrophages and dendritic cells arising from the donor bone marrow serve as antigen-presenting cells in the thymus to eliminate donor reactive host lymphocytes. In addition to this "central tolerance", other peripheral immunoregulatory mechanisms, such as clonal anergy and immune suppression, appear to contribute to the overall tolerance observed in mixed hematopoietic chimeras.

Establishment of MAHC using BMT suffers from three major obstacles; graft-versus-host (GVH) reaction, host-versus-graft (HVG) reaction, and stem cell competition. GVH reactions are primarily mediated by mature donor T cells in the transplanted bone marrow inoculum that recognize host alloantigens and mount an immune response, resulting in graft-versus-host disease (GVHD). GVHD affects many organs and often yields life threatening com-

TABLE 1

SA-FasL works in synergy with rapamycin to prevent allograft rejection.

| Grp | Donor | Recipient | Soluble proteins | Rapamycin (mg/kg) | N | Graft Survival |
|---|---|---|---|---|---|---|
| 1 | BALB/c | C57BL/6 | None | None | 4 | 7, 8, 8, 8 |
| 2 | BALB/c | C57BL/6 | None | 0.2 daily for 15 doses | 4 | 17, 20, 20, 22 |
| 4 | BALB/c | C57BL/6 | SA-FasL 1 µg, iv, daily for 15 days | 0.2 daily for 15 doses | 6 | >70, >70, >100, >100, >100, >100 |

Figure 8:
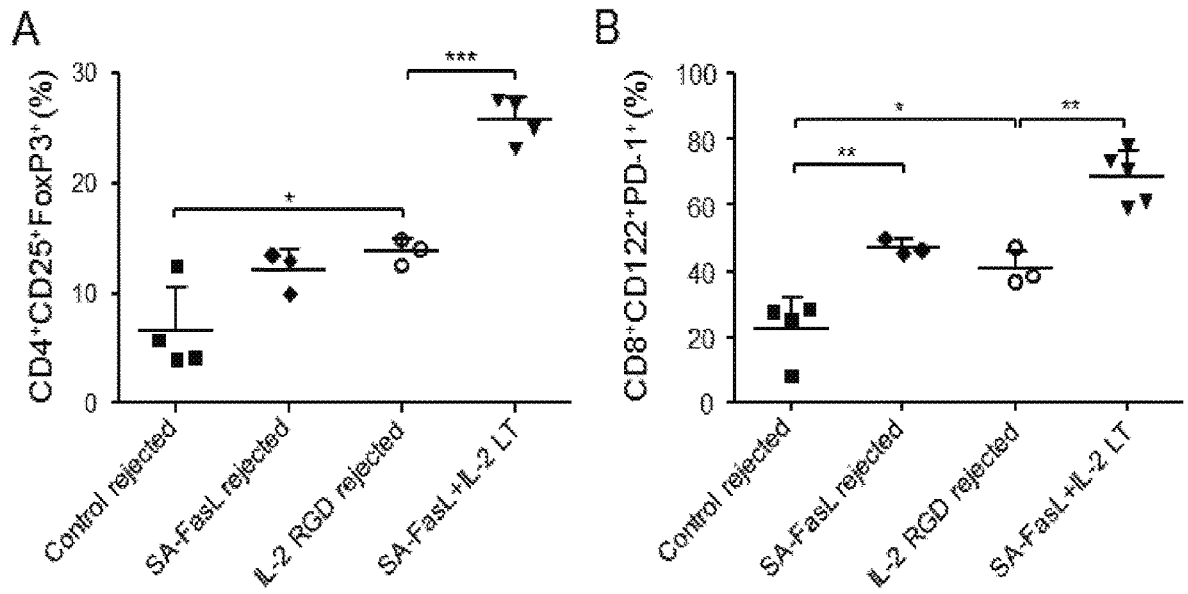
FIG. 8. Increased $CD4^+CD25^+FoxP3^+$ and $CD8^+CD122^+PD1^+$ T reg cells within the graft. Frequencies of $CD4^+CD25^+FoxP3^+$ and $CD8^+CD122^+PD1^+$ Treg cells within heart grafts at rejection or experimental end-point (LT; >100 days) shown as percentage of total $CD4^+$ (A) and $CD8^+$ T (B) cells.
Figure 9:
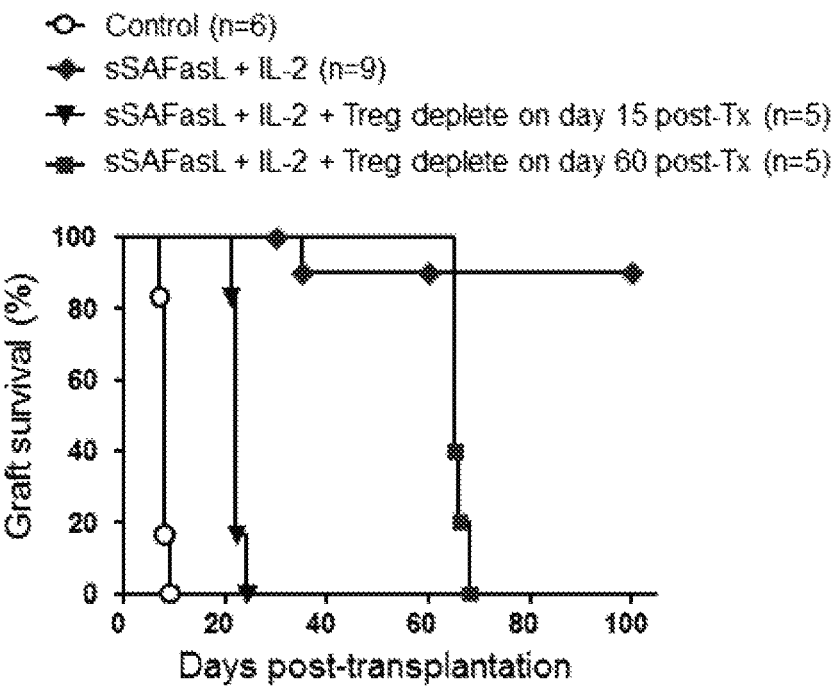
FIG. 9. $CD4^+CD25^+FoxP3^+$ Treg cells are important to tolerance induced by SA-FasL+IL-2. C57BL/6.FoxP3$^{DTR}$ recipients of allogeneic BALB/c hearts were treated with IL-2 and SA-FasL regimen used in FIG. 7 to induce tolerance. Mice were injected i.p. with two doses of 50 ng/kg diphtheria toxin (DT) on two consecutive days to deplete Treg cells expressing DT receptor under the control of FoxP3. Treg depletion was confirmed by flow cytometry and mice were monitored for graft survival.
Figure 10:
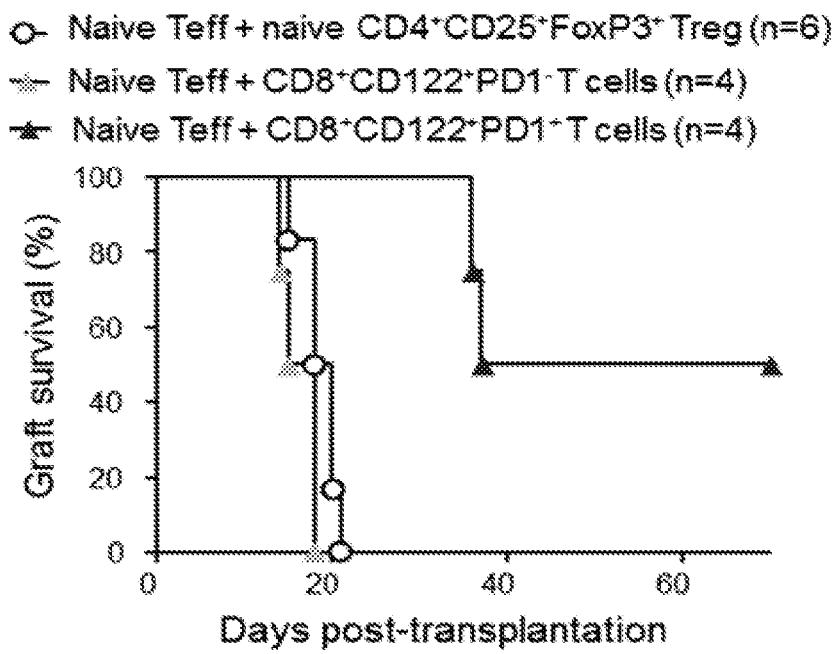
FIG. 10. $CD8^+CD122^+PD1^+$ T cells have regulatory function. $CD8^+CD122^+PD1^+$ and $CD8^+CD122^+PD1^-$ cells were flow sorted from long-term heart grafts infiltrating lymphocytes and $5\times10^3$ cells from each population was co-transferred with $1\times10^6$ flow sorted naïve spleen $CD4^+CD25^-$ Teff cells into Rag$^{-/-}$ mice. One day later, these animals were transplanted with BALB/c hearts and graft rejection was monitored. Animals receiving flow sorted naïve Teff cells and naïve $CD4^+CD25^+FoxP3^+$ (GFP) cells served as controls.

Mechanistic studies demonstrated a higher frequency of both CD4$^+$CD25$^+$FoxP3$^+$ Treg as well as CD8$^+$CD122$^+$PD-1$^+$ T cells in graft draining lymph node (not shown) and heart graft (FIG. 8). Depletion of CD4$^+$CD25$^+$FoxP3$^+$ Treg cells 15 or 60 days after transplantation negated the tolerogenic effect of SA-FasL and IL-2 and resulted in prompt graft rejection (FIG. 9). CD8$^+$CD122$^+$PD-1$^+$ T cells had regulatory function as i) depletion of these cells in long-term mice (>100 days) resulted in graft rejection in ~50% of recipients, and ii) flow cytometry sorted CD8$^+$CD122$^+$PD-1$^+$, but not CD8$^+$CD122$^+$PD-1$^-$, T cells prevented rejection of BALB/c hearts in an adoptive transfer model using Rag KO mice (FIG. 10).

plications. Although depletion of mature T cells from BM grafts is effective in preventing GVHD, it is associated with a high incidence of engraftment failure. Current treatment for GVHD involves nonspecific immunosuppression using various agents. However, although somewhat effective in preventing GVHD, the chronic use of these agents is associated with increase incidences of secondary malignancies and infections.

Rejection of allogeneic BMC by the host mature T cells represents a second hurdle that needs to be overcome in order to establish mixed chimerism. A series of approaches have been implemented to physically and functionally eliminate host T cells reactive to donor BMC for the establishment of mixed chimerism. These regimens mostly rely on nonspecific immunosuppressive regimens or generalized lymphocyte-specific interventions. All of these approaches can potentially render the host immunoincompetent. Therefore, it is important to develop clinically applicable protocols that are more effective, specific for the elimination of pathogenic T cells, and involves minimal conditioning of the host.

The third important barrier for the establishment of mixed hematopoietic chimerism is the competition between the donor and host HSC for available niches. In order to facilitate engraftment, most mixed chimerism protocols developed to date rely on host preconditioning to achieve some level of host HSC depletion. Total body irradiation has been the method of choice because of its reproducibility and ease of administration.

Figure 11A:
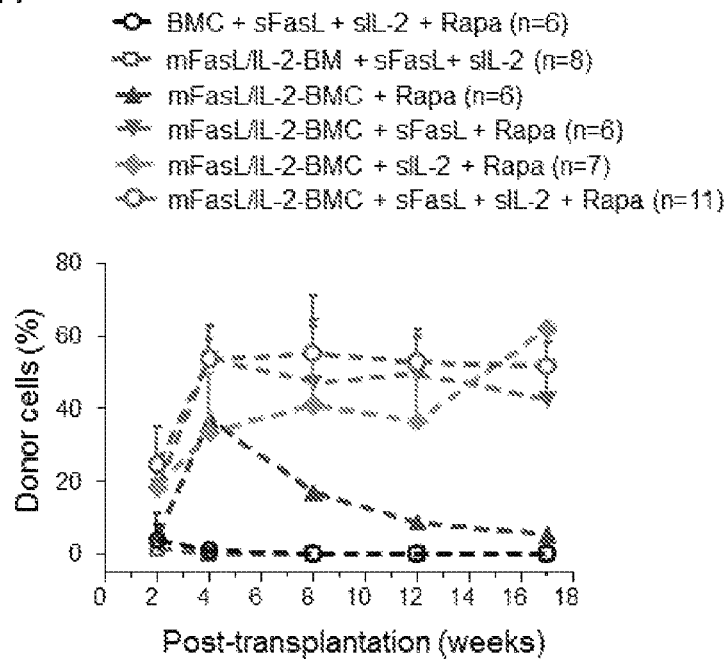
FIG. 11A-C. SA-FasL and IL-2 combination as an effective means of establishing mixed hematopoietic allogeneic chimerism. C57BL/6 mice were subjected to 300 cGy total body irradiation followed by intravenous transplantation of $30\times10^6$ unmodified (BMC) or SA-FasL (mFasL-BMC) or the combination of SA-FasL and SA-IL-2 (mFasL/IL-2-BMC) one day later. Selected groups of mice were also treated i.p. with 500 ng/daily for 15 doses of soluble SA-FasL (sFasL), 25,000 IU/daily for 7 doses of soluble IL-2 (sIL-2; human IL-2 obtained commercially or produced in house using insect cells transfected with human IL-2 cDNA engineered to include a 6xHis tag (SEQ ID NO: 11) for purification) or combination of both molecules (sFasL+sIL-2). The indicated groups also were treated i.p. with 10 daily doses of rapamycin at 0.5 mg/kg. Percent donor chimerism at various times post-transplantation was assessed using peripheral blood lymphocytes with antibodies against donor class I MHC molecule in flow cytometry.
Figure 11B:
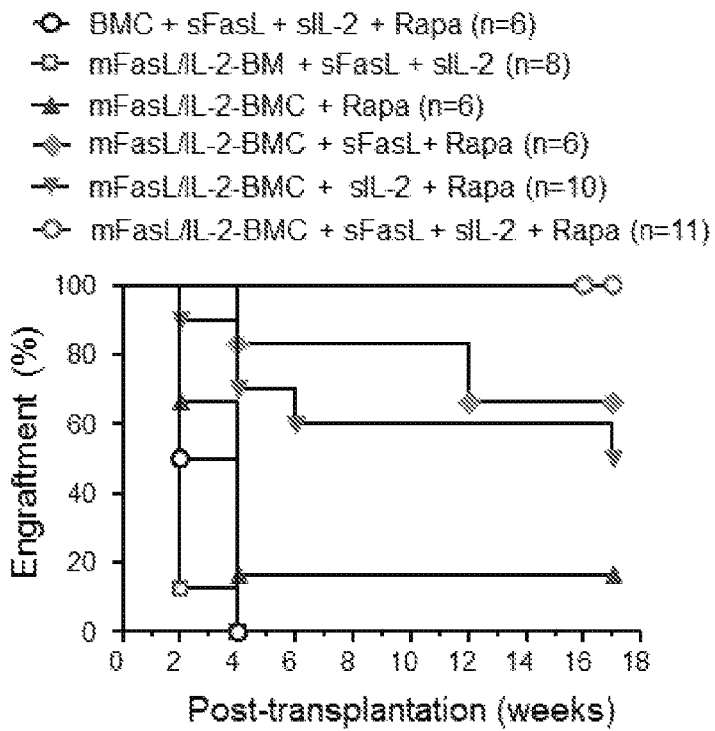
Figure 11C:
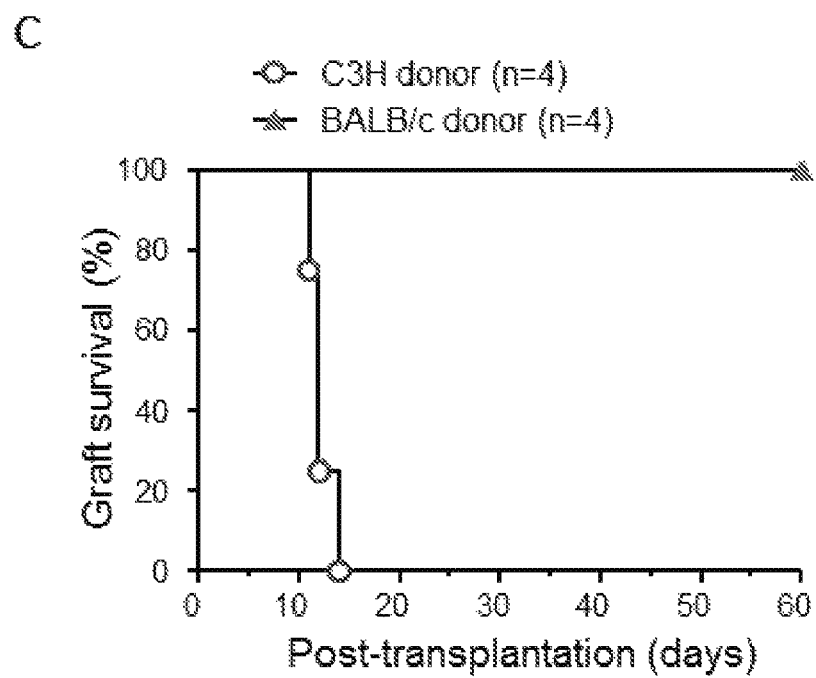

The efficacy of combined use of soluble SA-FasL and IL-2 in inducing tolerance to allogeneic pancreatic islets as tissue graft led us to test if this regimen is also effective in inducing tolerance to a solid organ. C57BL/6 mice were subjected to 300 cGy total body irradiation followed by intravenous transplantation of $30 \times 10^6$ unmodified (BMC) or SA-FasL (mFasL-BMC) or the combination of SA-FasL and SA-IL-2 (mFasL/IL-2-BMC) one day later. FIG. 11 A-C. Selected groups of mice were also treated i.p. with 500 ng/daily for 15 doses of soluble SA-FasL (sFasL), 25,000 IU/daily for 7 doses of soluble IL-2 (sIL-2; human IL-2 obtained commercially or produced in house using insect cells transfected with human IL-2 cDNA engineered to include a 6xHis tag (SEQ ID NO: 11) for purification) or combination of both molecules (sFasL+sIL-2). The indicated groups also were treated i.p. with 10 daily doses of rapamycin at 0.5 mg/kg. Percent donor chimerism at various times post-transplantation was assessed using peripheral blood lymphocytes with antibodies against donor class I MHC molecule in flow cytometry. FIG. 11A, average donor chimerism, FIG. 11B, percent engraftment, FIG. 11C, Long-term chimeric mice reject C3H third-party, but not BALB/c donor skin, demonstrating donor-specific tolerance.

These data demonstrated that the generation of durable mixed allogeneic chimerism in mice pretreated with 300 cGy total body irradiation required both SA-FasL/IL-2 attached to the surface of BM cells as well as systemic treatment of recipients either with soluble SA-FasL or IL-2. However, the systemic use of both molecules as biologics improved the efficacy of percent donor chimerism as well as engraftment because all the recipients were successfully engrafted. Importantly, long-term chimeric mice were immunocompetent and tolerant to donor antigens as they rejected third party, but not donor, skin grafts. Therefore, the combined use of SA-FasL and IL-2 improves long-term transplant tolerance.

Figure 12A:
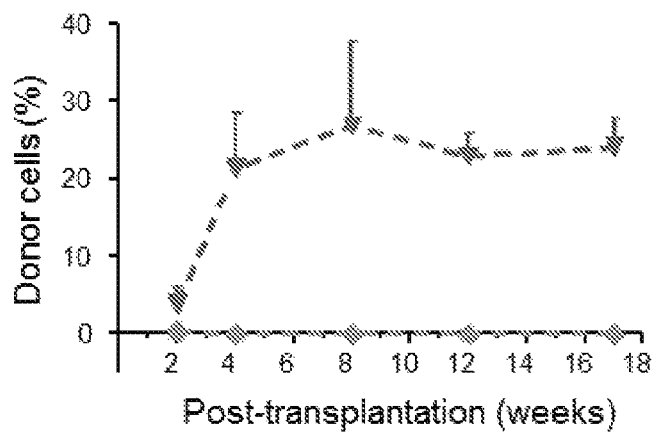
FIG. 12A-C. Cyclophosphamide works in synergy with SA-FasL and IL-2 combination in establishing mixed hematopoietic allogeneic chimerism. C57BL/6 mice were subjected to 100 cGy total body irradiation followed by intravenous transplantation of $30\times10^6$ unmodified (BMC) or the combination of SA-FasL and SA-IL-2 (mFasL/IL-2-BMC) one day later. Selected groups of mice were also treated i.p. with cyclophosphamide (200 mg/kg) on day+2. All groups were treated i.p. with rapamycin (2 mg/kg) daily for 10 doses starting on day 6 pot-transplantation. The test group was also treated starting on day 6 post-transplantation with both soluble SA-FasL (sFasL; 500 ng/daily for 15 doses) and IL-2 (25,000 IU/daily for 7 doses). Percent donor chimerism at various times post-transplantation was assessed using peripheral blood lymphocytes with antibodies against donor class I MHC molecule in flow cytometry.

Example 8 Cyclophosphamide Worked in Synergy with the SA-FasL and IL-2 Combination to Establish Mixed Hematopoietic Allogeneic Chimerism We further tested whether other immunomodulatory agents such as cyclophosphamide can further improve the effect of SA-FasL and IL-2 in establishing mixed hematopoietic allogeneic chimerism when low dose of total body irradiation is used. C57BL/6 mice were subjected to 100 cGy total body irradiation followed by intravenous transplantation of $30 \times 10^6$ unmodified (BMC) or the combination of SA-FasL and SA-IL-2 (mFasL/IL-2-BMC) one day later. Selected groups of mice were also treated i.p. with cyclophosphamide (200 mg/kg) on day+2. All groups were treated i.p. with rapamycin (2 mg/kg) daily for 10 doses starting on day 6 pot-transplantation. The test group was also treated starting on day 6 post-transplantation with both soluble SA-FasL (sFasL; 500 ng/daily for 15 doses) and IL-2 (25,000 IU/daily for 7 doses). Percent donor chimerism at various times post-transplantation was assessed using peripheral blood lymphocytes with antibodies against donor class I MHC molecule in flow cytometry. FIG. 12A, average donor chimerism, FIG. 12B, percent engraftment, FIG. 12C, long-term chimeric mice reject C3H third-party, but not BALB/c donor skin, demonstrating donor-specific tolerance. Nonchimeric control mice (BMC+cyclophosphamide+rapamycin) rejected grafts from both donor and third party (data not shown).

These data demonstrated that cyclophosphamide acted synergistically in combination with SA-FasL and IL-2 to establish mixed hematopoietic allogeneic chimerism. Furthermore, analysis of various tissues from mice with durable donor mixed chimerism revealed that the treatment induced long-term multilineage donor chimerism (FIG. 13A-B).

Figure 12B:
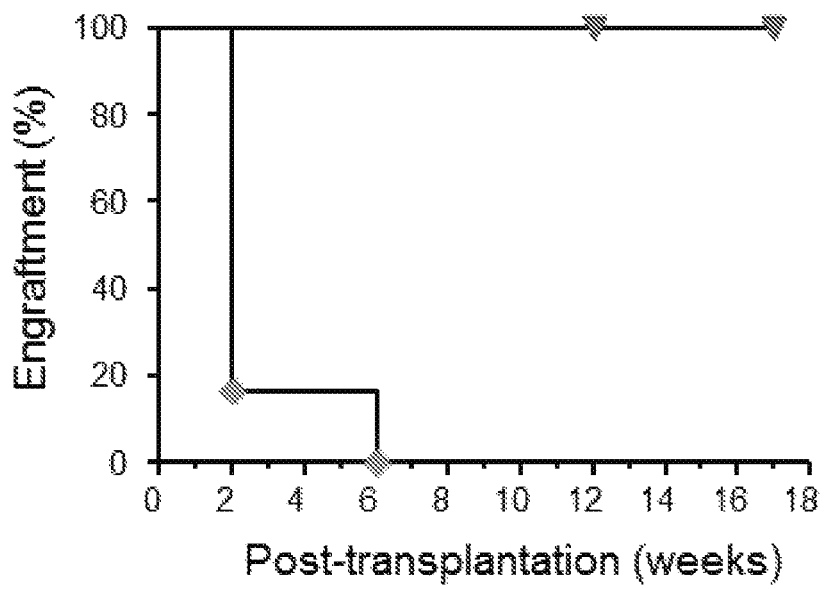
Figure 12C:
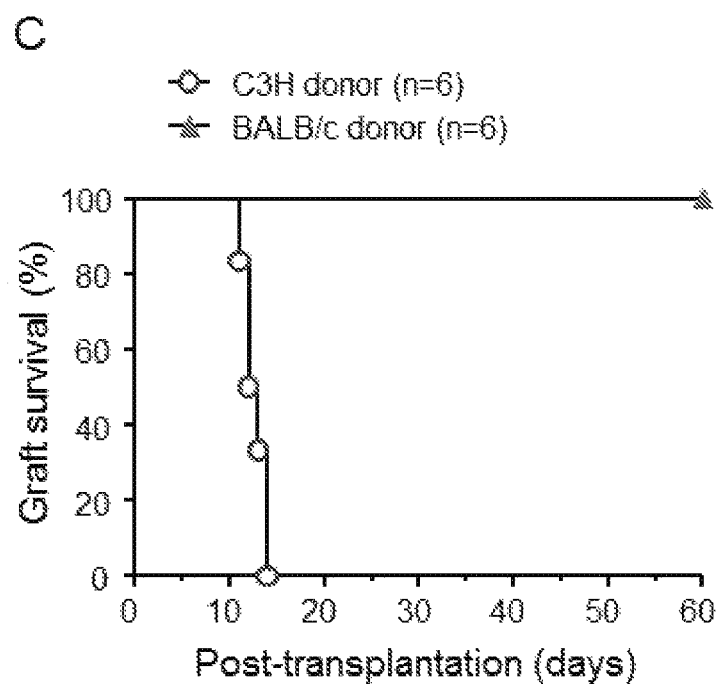

Example 9 Mice with Durable Donor Mixed Chimerism Generate In Vitro Response to Third Party, but not Donor Alloantigens To further test the immunocompetence of mice having established durable donor mixed chimerism after transplantation, spleens were harvested from long-term (>100 days) durable mixed chimeras and control mice that rejected donor BMCs shown in FIG. 12A-B. Spleens were processed into single cell suspension, labeled with 2.5 µM CFSE, resuspended in DMEM, and $50 \times 10^6$ CFSE labeled splenocytes were plated on a petri dish for 45 minutes at 37° C. to enrich lymphocytes. After 45 minutes non-adherent cells were collected, washed, and incubated ($1 \times 10^5$ cells) with irradiated (2000 cGy; $1 \times 10^5$ cells) donor BALB/c or C3H splenocytes as stimulators in 96-well U-bottom titer plates in mixed lymphocyte reaction medium. Irradiated syngeneic C57BL/6 cells were used as controls. After 4 days, cells were stained with fluorochrome-labeled antibodies against rat CD4 and CD8, analyzed by flow cytometry gating on live cells, and the percentage of proliferating cells is graphed. As demonstrated by the data in FIG. 14, long-term chimeric animals generated a proliferative response to C3H third party stimulators, but not BALB/c donor antigens, demonstrating immune competence and antigen-specific tolerance. In marked contrast, lymphocytes from nonchimeric mice generated a proliferative response to both C3H third party as well as BALB/c stimulators, demonstrating lack of antigen-specific tolerance.

What is claimed is:

1. A method of inducing immune tolerance in a subject in need thereof, comprising administering to the subject (i) a chimeric FasL protein comprising a FasL moiety and a streptavidin or avidin moiety and (ii) an IL-2 protein, wherein the chimeric FasL protein and the IL-2 protein are administered in separate compositions sequentially in any order or substantially simultaneously or are administered in the same composition.

2. The method of claim 1, wherein:
the chimeric FasL protein is administered in a form selected from the group consisting of soluble chimeric FasL proteins comprising a FasL moiety and a streptavidin or avidin moiety and chimeric FasL-decorated cells comprising a chimeric FasL protein comprising a FasL moiety and an streptavidin or avidin moiety bound to a cell surface via a biotin moiety on the cell surface; and
the IL-2 protein is administered in a form selected from the group consisting of soluble IL-2 proteins, soluble chimeric IL-2 proteins comprising an IL-2 moiety and a streptavidin or avidin moiety; and chimeric IL-2-decorated cells comprising a chimeric IL-2 protein comprising an IL-2 moiety and a streptavidin or avidin moiety bound to a cell surface via a biotin moiety on the cell surface.

3. The method of claim 2, comprising administering (i) soluble chimeric FasL protein and (ii) soluble IL-2 protein or soluble chimeric IL-2 protein, in separate compositions sequentially in any order or substantially simultaneously, or in the same composition.

4. The method of claim 2, comprising administering (i) chimeric FasL-decorated cells and (ii) soluble IL-2 protein or soluble chimeric IL-2 protein, in separate compositions sequentially in any order or substantially simultaneously, or in the same composition.

5. The method of claim 2, comprising administering (i) soluble chimeric FasL protein, and (ii) chimeric IL-2-decorated cells, in separate compositions sequentially in any order or substantially simultaneously, or in the same composition.

6. The method of claim 2, comprising administering (i) chimeric FasL-decorated cells and (ii) chimeric IL-2-decorated cells, in separate compositions sequentially in any order or substantially simultaneously, or in the same composition.

7. The method of claim 2, wherein:
the subject is in need of treatment for type 1 diabetes and the decorated cells, if present, are PBMCs, bone marrow cells, hematopoietic stem cells, stem cells, mesenchymal stem cells, dendritic cells, dendritic cells pulsed with autoantigens, human beta cell products, or splenocytes; or
the subject is in need of the treatment or prevention of allograft rejection and the decorated cells, if present, are cells of the allograft selected from the group consisting of allograft bone marrow cells, hematopoietic stem cells, stem cells, dendritic cells, mesenchymal stem cells, cardiac myocytes and vascular cells.

8. The method of claim 1, wherein the chimeric FasL protein has the amino acid sequence of SEQ ID NO: 3.

9. The method of claim 1, wherein the chimeric IL-2 protein has the amino acid sequence of SEQ ID NO: 9.

* * * * *

UNITED STATES PATENT AND TRADEMARK OFFICE
CERTIFICATE OF CORRECTION

| | | |
|---|---|---|
| PATENT NO. | : 12,023,367 B2 | Page 1 of 1 |
| APPLICATION NO. | : 15/736088 | |
| DATED | : July 2, 2024 | |
| INVENTOR(S) | : Haval Shirwan | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1445 days.

Signed and Sealed this
Eighth Day of October, 2024

Katherine Kelly Vidal
*Director of the United States Patent and Trademark Office*